(12) United States Patent
Bringhurst et al.

(10) Patent No.: US 6,537,965 B1
(45) Date of Patent: Mar. 25, 2003

(54) AMINO-TERMINAL MODIFIED PARATHYROID HORMONE (PTH) ANALOGS

(75) Inventors: F. Richard Bringhurst, Walpole, MA (US); Hisashi Takasu, Mishima (JP); Thomas J. Gardella, Needham, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/447,800

(22) Filed: Nov. 23, 1999

Related U.S. Application Data
(60) Provisional application No. 60/110,152, filed on Nov. 25, 1998.

(51) Int. Cl.$^7$ .......................... A61K 38/00; A61K 45/00; A61K 39/00; C12P 21/08; A61M 36/14

(52) U.S. Cl. .............................. 514/2; 514/12; 514/13; 424/1.11; 424/85.1; 424/198.1; 530/324; 530/300; 530/399; 530/388.22; 530/326

(58) Field of Search .................................. 530/399, 300, 530/324, 388.22, 326; 536/23.51, 23.1; 435/35, 320.1, 325, 252.3; 424/85.1, 198.1, 1.11; 514/2

(56) References Cited

U.S. PATENT DOCUMENTS

| | | | | |
|---|---|---|---|---|
| 4,423,037 A | * | 12/1983 | Rosenblatt et al. | .......... 424/177 |
| 4,698,328 A | * | 10/1987 | Neer et al. | ...................... 514/12 |
| 5,350,836 A | * | 9/1994 | Kopchick et al. | ............ 530/399 |
| 6,066,618 A | | 5/2000 | Holick | .......................... 514/12 |

FOREIGN PATENT DOCUMENTS

| | | | | |
|---|---|---|---|---|
| JP | 58-96052 | * | 1/1983 | .......... A61K/37/24 |
| JP | 59-204159 | * | 1/1984 | .......... C07C/103/52 |

OTHER PUBLICATIONS

Smith, T.F. and Zhang, X. (1997) The challenges of genome sequence annotation or "The devil is in the details", Nature Biotechnology, 15: 1222–1223.*

Brenner, S. (1999) Errors in genome annotation, Trends in Genetics, 15(4): 3–4, esp. Fig. 2.*

Wells, J.A. (1990) Additivity of mutational effects in proteins. Biochem, 29(37): 8509–8517, esp. Table II.*

Abou–Samra, A.–B., et al., "Expression cloning of a common receptor for parathyroid hormone and parathyroid hormone–related peptide from rat osteoblast–like cells: A single receptor stimulates intracellular accumulation of both cAMP and inositol triphosphates and increases intracellular free calcium," *PNAS USA* 89:2732–2736 (Apr. 1992).

Azarani, A., et al., "Structurally Diverse N–terminal Peptides of Parathyroid Hormone (PTH) and PTH–related Peptide (PTHRP) Inhibit the $NA^+/H^+$ Exchanger NHE3 Isoform by Binding to the PTH–PTHRP Receptor Type I and Activating Distinct Singaling Pathways," *J. Biol. Chem.* 271:14931–14936 (Jun. 1996).

Bos, M.P., et al., "Expression of the Parathyroid Hormone Receptor and Correlation with Other Osteoblastic Parameters in Fetal Rat Osteoblasts," *Calcif. Tisse Int.* 58:95–100 (Feb. 1996).

Bringhurst, F.R., et al., "Cloned, Stably Expressed Parathyroid Hormone (PTH)/PTH–Related Peptide Receptors Activate Multiple Messenger Signals and Biological Responses in $LLC-PK_1$ Kidney Cells," *Endocrinol.* 132:2090–2098 (May 1993).

Chakravarthy, B.R., et al., "Parathyroid Hormone Fragment [3–34] Stimulates Protein Kinase C (PKC) Activity in Rat Osteosarcoma and Murine T–Lymphoma Cells," *Biochem. Biophys. Res. Comm.* 171:1105–1110 (Sep. 1990).

Civitelli, R., et al., "PTH elevates inositol polyphosphates and diacylglycerol in a rat osteoblast–like cell line," *Am. J. Physiol.* 255:E660–E667 (Nov. 1988).

Cole, J.A., et al., "Regulation of Sodium–Dependent Phosphate Transport by Parathyroid Hormone in Opossum Kidney Cells: Adenosine 3', 5'–Monophosphate–Dependent and –Independent Mechanisms," *Endocrinol.* 122:2981–2989 (Jun. 1988).

Donahue, H.J., et al., "Differential Effects of Parathyroid Hormone and Its Analogues on Cytosolic Calcium Ion and cAMP Levels in Cultured Rat Osteoblast–like Cells," *J. Biol. Chem.* 263:13522–13527 (Sep. 1988).

Dunlay, R., and Hruska, K., "PTH receptor coupling to phospholipase C is an alternate pathway of signal transduction in bone and kidney," *Am. J. Physiol.* 258:F223–F231 (Feb. 1990).

Fujimori, A., et al., "Dissociation of Second Messenger Activation by Parathyroid Hormone Fragments in Osteosarcoma Cells," *Endocrinol.* 128:3032–3039 (Jun. 1991).

(List continued on next page.)

Primary Examiner—Elizabeth Kemmerer
Assistant Examiner—Sandra Wegert
(74) *Attorney, Agent, or Firm*—Sterne, Kessler, Goldstein & Fox P.L.L.C.

(57) ABSTRACT

Disclosed are novel parathyroid hormone (PTH) peptide derivatives. In particular, the invention relates to PTH derivatives having amino acid substitutions that confer PTH-1/PTH-2 receptor agonist or antagonist properties to the derivatives. Also disclosed are methods of preparing these novel derivatives, and methods of using these derivatives to treat mammalian conditions.

6 Claims, 6 Drawing Sheets

OTHER PUBLICATIONS

Fujimori, A., et al., "Structure–Function Relationship of Parathyroid Hormone: Activation of Phospholipase–C, Protein Kinase–A and –C in Osteosarcoma Cells," *Endocrinol.* 130:29–36 (Jan. 1992).

Gardella, T.J., et al., "Analysis of Parathyroid Hormone's Principal Receptor–Binding Region by Site–Directed Mutagenesis and Analog Design," *Endocrinol.* 132:2024–2030 (May 1993).

Goltzmann, D., et al., "Analysis of the Requirements for Parathyroid Hormone Action in Renal Membranes with the Use of Inhibiting Analogues," *J. Biol. Chem.* 250:3199–3203 (Apr. 1975).

Goud, N.A., et al., "Sold–Phase Synthesis and Biologic Activity of Human Parathyroid Hormone (1–84)," *J. Bone Min. Res.* 6:781–789 (Aug. 1991).

Guo, J., et al., "Parathyroid Hormone (PTH)/PTH–Related Peptide Receptor Density Modulates Activation of Phospholipase C and Phosphate Transport by PTH in LLC–PK1 Cells," *Endocrinol.* 136:3884–3891 (Sep. 1995).

Hilliker, S., et al., "Truncation of the Amino Terminus of PTH Alters Its Anabolic Activity on Bone In Vivo," *Bone* 19:469–477 (Nov. 1996).

Iida–Klein, A., et al., "Mutations in the Second Cytoplasmic Loop of the Rat Parathyroid Hormone (PTH)/PTH–related Protein Receptor Result in Selective Loss of PTH–stimulated Phospholpiase C Activity," *J. Biol. Chem.* 272:6882–6889 (Mar. 1997).

Inomata, N., et al., "Characterization of a Novel Parathyroid Hormone (PTH) Receptor with Specificity for the Carboxyl–Terminal Region of PTH–(1–84)," *Endocrinol.* 136:4732–4740 (Nov. 1995).

Janulis, M., et al., "Structure–Function Requirements of Parathyroid Hormone for Stimulation of 1,25–Dihydroxyvitamin $D_3$ Production by Rat Renal Proximal Tubules," *Endocrinol.* 133:713–719 (Aug. 1993).

Jobert, A.–S., et al., "Parathyroid Hormone–Induced Calcium Release from Intracellular Stores in a Human Kidney Cell Line in the Absence of Stimulation of Cyclic Adenosine 3',5'–Monophosphate Production," *Endocrinol.* 138:5282–5292 (Dec. 1997).

Jouishomme, H., et al., "The Protein Kinase–C Activation Domain of the Parathyroid Hormone," *Endocrinol.* 130:53–60 (Jan. 1992).

Jouishomme, H., et al., "Further Definition of the Protein Kinase C Activation Domain of the Parathyroid Hormone," *J. Bone Min. Res.* 9:943–949 (Jun. 1994).

Jüppner, H., et al., "A G Protein–Linked Receptor for Parathyroid Hormone and Parathyroid Hormone–Related Peptide," *Science* 254:1024–1026 (Nov. 1991).

Kimura, T., et al., "Strategy for the Synthesis of Large Peptides: An Application to the Total Synthesis of Human Parathyroid Hormone [hPTH(1–84)]," *Biopolymers* 20:1823–1832 (Sep. 1981).

Kronenberg, H.M., et al., "The PTH/PTHrP Receptor: One Receptor for Two Ligands," in *Molecular Genetics of Endocrine Disorders*, Thakker, R.V., ed., Chapman & Hall Medical, publ., London, England, pp. 389–420 (1997).

Murray, T.M., et al., "Dexamethasone–Treated ROS 17/2.8 Rat Osteosarcoma Cells are Responsive to Human Carboxylterminal Parathyroid Hormone Peptide hPTH (53–84): Stimulation of Alkaline Phosphatase," *Calcif. Tissue Int.* 49:120–123 (Aug. 1991).

Neugebauer, W., et al., "Solution Structure and Adenylyl Cyclase Stimulating Activities of C–Terminal Truncated Human Parathyroid Hormone Analogues," *Biochem.* 34:8835–8842 (Jul. 1995).

Orloff, J.J., et al., "Analysis of PTHRP binding and signal transduction mechanisms in benign and malignant squamous cells," *Am. J. Physiol.* 262:E599–E607 (May 1992).

Parsons, J.A., et al., "Pharmacology of parathyroid hormone and some of its fragments and analogues," in *Calcium–regulating hormones. Proceedings of the Fifth Parathyroid Conference, Oxford, United Kingdom, Jul. 21–26, 1974*, Talmage, R.V., et al., eds., American Elsevier Publishing Co., Inc., New York, NY, pp. 33–39 (1975).

Pines, M., et al., "Generation and Characterization of Human Kidney Cell Lines Stably Expressing Recombinant Human PTH/PTHrP Receptor: Lack of Interaction with a C–Terminal Human PTH Peptide," *Endocrinol.* 135:1713–1716 (Oct. 1994).

Pines, M., et al., "Inositol 1–,4–,5–Trisphosphate–Dependent $Ca^{2+}$ Signaling by the Recombinant Human PTH/PTHrP Receptor Stably Expressed in a Human Kidney Cell Line," *Bone* 18:381–389 (Apr. 1996).

Reid, I.R., et al., "Parathyroid hormone acutely elevates intracellular calcium in osteoblastlike cells," *Am. J. Physiol.* 253:E45–E51 (Jul. 1987).

Rixon, R.H., et al., "Parathyroid Hormone Fragments May Stimulate Bone Growth in Ovariectomized Rats by Activating Adenylyl Cyclase," *J. Bone Min. Res.* 9:1179–1189 (Aug. 1994).

Schipani, E., et al., "Identical Complementary Deoxyribonucleic Acids Encode a Human Renal and Bone Parathyroid Hormone (PTH)/PTH–Related Peptide Receptor," *Endocrinol.* 132:2157–2165 (May 1993).

Schneider, H., et al., "Cloning and functional expression of a human parathyroid hormone receptor," *Eur. J. Pharmacol.* 246:149–155 (Jul. 1993).

Schneider, H., et al., "A C–terminally truncated human parathyroid hormone receptor is functional and activates multiple G proteins," *FEBS Letts.* 351:281–285 (Sep. 1994).

Segre, G.V., et al., "Characterization of Parathyroid Hormone Receptors in Canine Renal Cortical Plasma Membranes Using a Radioiodinated Sulfur–free Hormone Analogue," *J. Biol. Chem.* 254: 6980–6986 (Aug. 1979).

Seuwen, K., and Boddeke, H.G.W.M., "Heparin–insensitive calcium release from intracellular stores triggered by the recombinant human parathyroid hormone receptor," *Br. J. Pharmacol.* 114:1613–1620 (Apr. 1995).

Shukunami, C., et al., "Chondrongenic Differentiation of Clonal Mouse Embryonic Cell Line ATDC5 In Vitro: Differentiation–dependent Gene Expression of Parathyroid Hormone (PTH)/PTH–related Peptide Receptor," *J. Cell Biol.* 133:457–468 (Apr. 1996).

Siegfried, G., et al., "Parathyroid Hormone Stimulates Ecto–5'–Nucleotidase Activity in Renal Epithelial Cells: Role of Protein Kinase–C," *Endocrinol.* 136:1267–1275 (Mar. 1995).

Takasu, H., et al., "The 69–84 Amino Acid Region of the Parathyroid Hormone Molecule Is Essential for the Interaction of the Hormone with the Binding Sites with Carboxyl–Terminal Specificity," *Endocrinol.* 137:5537–5543 (Dec. 1996).

Takasu, H., and Bringhurst, F.R., "Type–1 Parathyroid Hormone (PTH)/PTH–Related Peptide (PTHrP) Receptors Activate Phospholipase C in Response to Carboxyl–Truncated Analogs of PTH(1–34)," *Endocrinol. 139*:4293–4299 (Oct. 1998).

Takasu, H. et al., "Human PTH/PTHrP receptors and Type–2 PTH Receptors Show Discordant Selectivity for Human PTH Analogs with Amino–Terminal Modifications," *Bone* 23:S255, Abstract No. T223 (Nov. 1998).

Takasu, H., et al., "Dual Signaling and Ligand Selectivity of the Human PTH/PTHrP Receptor," *J. Bone Min. Res. 14*:11–20 (Jan. 1999).

Takasu, H. et al., "Amino–Terminal Modifications of Human Parathyroid Hormone (PTH) Selectively Alter Phospholipase C Signaling via the Type 1 PTH Receptor: Implications for Design of Signal–Specific PTH Ligands," *Biochem. 38*:13453–13460 (Oct. 1999).

Tamura, T., et al., "Parathyroid Hormone 1–34, But Not 3–34 or 7–34, Transiently Translocates Protein Kinase C in Cultured Renal (OK) Cells," *Biochem. Biophys. Res. Comm. 159*:1352–1358 (Mar. 1989).

Tregear, G.W., et al., "Bovine Parathyroid Hormone: Minimum Chain Length of Synthetic Peptide Required for Biological Activity," *Endocrinol. 93*:1349–1353 (Dec. 1973).

Tregear, G.W., and Potts, Jr., J.T., "Synthetic Analogues of Residues 1–34 of Human Parathyroid Hormone: Influence of Residue Number 1 on Biological Potency In Vitro," *Endocrine Res. Comm. 2*:561–570 (1975).

Usdin, T.B., et al., "Identification and Functional Expression of a Receptor Selectively Recognizing Parathyroid Hormone, the PTH2 Receptor," *J. Biol. Chem. 270*:15455–15458 (Jun. 1995).

Whitfield, J.F., and Morley, P., "Small bone–building fragments of parathyroid hormone: new therapeutic agents for osteoporosis," *Trends Pharmacol. Sci. 16*:382–386 (Nov. 1995).

Yamamoto, S., et al., "Parathyroid Hormone–Related Peptide–(1–34) [PTHrP–(1–34)] Induces Vasopressin Release from the Rat Supraoptic Nucleus in Vitro through a Novel Receptor Distinct from a Type I or Type II PTH/PTHrP Receptor," *Endocrinol. 138*:2066–2072 (May 1997).

* cited by examiner

AMINO-TERMINAL MODIFIED PARATHYROID HORMONE (PTH) ANALOGS

This application claims the benefit of the filing date of provisional application 60/110,152 filed on Nov. 25, 1998, which is herein incorporated by reference.

Statement as to Rights to Inventions Made Under Federally-Sponsored Research and Development Part of the work performed during development of this invention utilized U.S. Government funds. The U.S. Government has certain rights in this invention.

This work was supported by National Institutes of Health Grant DK 1 1794.

BACKGROUND OF THE INVENTION

1. Field of the Invention

The present invention relates to novel parathyroid hormone peptide (PTH) derivatives. In particular, the invention relates to PTH derivatives having one or more amino acid substitutions that confer PTH-1/PTH-2 receptor agonist or antagonist properties to the derivatives.

2. Description of Related Art

Full understanding of the complex biological roles of parathyroid hormone (PTH) and efforts to utilize its therapeutic potential require dissection of the multiple signaling patterns and cellular pathways of action of the hormone. PTH binds and activates specific receptors in renal and osseous target cells that also recognize PTH-related peptide (PTHrP) (Kronenberg, H., et al., "The PTH/PTHrP receptor: one receptor for two ligands," in *Genetics of Endocrine and Metabolic Disorders*, Thakker, R., ed., Chapman & Hall, London (1997), pp. 389–420). In renal and osteoblastic cell lines, PTH triggers several parallel intracellular signaling responses, including activation of adenylyl cyclase (AC), protein kinase A (PKA), phospholipase C (PLC) and protein kinase C (PKC) and generation of second messengers such as cyclic AMP (cAMP), inositol trisphosphate ($IP_3$), diacylglycerol and increased cytosolic free calcium ($Ca_i^{++}$) (Abou-Samra, A. B., et al., *Proc. Natl. Acad. Sci. U.S.A.* 89(7):2732–2736 (1992); Azarani, A., et al., *J. Biol. Chem.* 271(25):14931–14936(1996); Bringhurst, F. R., et al., *Endocrinology* 132(5):2090–2098 (1993); Civitelli, R., et al., *Am. J. Physiol.* 255(5 Pt 1):E660–667 (1988); Donahue, H. J., et al., *J. Biol. Chem.* 263:13522–13527 (1988); Dunlay, R., and Hruska, K., *Am. J. Physiol.* 258(2 Pt 2):F223–231 (1990); Fujimori, A., et al., *Endocrinology* 128(6):3032–3039 (1991); Fujimori, A., et al., *Endocrinology* 130(1):29–36 (1992); Guo, J., et al., *Endocrinology* 136(9):3884–3891 (1995); Janulis, M., et al., *Endocrinology* 133:713–719 (1993); Jouishomme, H., et al., *J. Bone Miner. Res.* 9(6):943–949 (1994); Juppner, H., et al., *Science* 254(5034):1024–1026 (1991); Pines, M., et al., *Bone* 18(4):381–389 (1996); Seuwen, K., et al., *Brit. J. Pharm.* 114(8):1613–1620 (1995); Siegfried, G., et al., *Endocrinology* 136(3):1267–1275 (1995).

To date, two structurally related but distinct species of PTH receptors have been cloned (Abou-Samra, A. B., et al., *Proc. Natl. Acad. Sci. U.S.A.* 89(7):2732–2736 (1992); Usdin, T. B., et al., *J. Biol. Chem.* 270(26):15455–15458 (1995); Schipani, E., et al., *Endocrinology-*132(5):2157–2165 (1993)). The first of these, type A, was isolated from both bone and kidney cells and shown to transduce multiple signaling responses to PTH-(1–34) or PTHrP-(1–36) when heterologously expressed in cells that lack endogenous type 1 PTH/PTHrP receptors (PTHRs) (Abou-Samra, A. B., et al., *Proc. Natl. Acad. Sci. U.S.A.* 89(7):2732–2736 (1992); Azarani, A., et al., *J. Biol. Chem.* 271(25):14931–14936 (1996); Bringhurst, F. R., et al., *Endocrinology* 132(5):2090–2098 (1993); Guo, J., et al., *Endocrinology* 136(9):3884–3891 (1995); Pines, M., et al., *Bone* 18(4):381–389 (1996); Jobert, A.-S., et al., *Endocrinology* 138(12):5282–5292 (1997); Schneider, H., et al., *Eur. J. Pharm.* 246(2):149–155 (1993)).

Previous efforts to define the contributions of specific regions of the PTH molecule to its binding and signaling properties have been undertaken mainly by use of complex in vivo bioassays, organ cultures, isolated cell membranes or cell lines, generally of rodent origin, that may express more than one type of endogenous PTH receptors (Janulis, M., et al., *Endocrinology* 133:713–719 (1993); Siegfried, G., et al., *Endocrinology* 136(3):1267–1275 (1995); Yamamoto, S., et al., *Endocrinology* 138:2066–2072 (1997); Jouishomme, H., et al., *Endocrinology* 130(1):53–60 (1992); Segre, G. V., et al., *J. Biol. Chem.* 254:6980–6986 (1979); Tregear, G. W., and Potts, J. T., Jr. *Endocr. Res. Commun.* 2:561–567 (1975); Takasu, H., et al., *Endocrinology* 137(12):5537–5543 (1996); Orloff, J. J., et al., *Am. J. Physiol.* 262(5 Pt 1):E599–607 (1992)). For example, relatively few modifications have been made to the extreme amino terminus of PTH: Synthetic [desamino-Ala-1]bPTH-(1–34) was disclosed by Tregear et al. (*Endocr. Res. Commun.* 2:561–570, page 566 (1975)), by Goltzmann et al. (*J. Biol. Chem.* 250:3199–3203, (1975)), and by Parsons et al. (Pharmacology of parathyroid hormone and some of its fragments and analogues. In: Talamage R V, Owen M, Parsons J. A. (Eds.) Calcium-Regulating Hormones. American Elsevier, New York, pp 33–39 (1975)); synthetic [desamino Ser$^1$]-hPTH(1–34) was disclosed by Tregear et al. (*Endocr. Res. Commun.* 2:561–570 (1975)) and by Rixon et al. (*J. Bone and Mineral Res.* 9: 1179–1189 (1994)); synthetic 1-desamino-hPTH-(1–31) was disclosed by Rixon et al. (*J. Bone and Mineral Res.* 9: 1179–1189, (1994))and synthetic [Ala$^1$]-hPTH(1–34), and [Gly$^1$]-hPTH(1–34) were disclosed by Tregear et al. (*Endocr. Res. Commun.* 2:561–570, page 563 (1975)).

Early structure/function studies of bovine PTH-(1–34), performed with isolated renal membranes, identified the key role of the carboxyl(C)-terminal bPTH-(25–34) region for receptor binding and of the amino(N)-terminus (i.e., Ser$^1$) for AC activation (Segre, G. V., et al., *J. Biol. Chem.* 254:6980–6986 (1979); Tregear, G. W., and Potts, J. T., Jr. *Endocr. Res. Commun.* 2:561–567 (1975)). Later work conducted in vitro with intact renal tubules or with cultured renal or bone cells, however, indicated that N-truncated analogs such as PTH-(3–34), although unable to stimulate AC, could fully activate PKC and could regulate certain PKC-dependent distal biologic responses (Janulis, M., et al., *Endocrinology* 133:713–719 (1993); Siegfried, G., et al., *Endocrinology* 136(3):1267–1275 (1995); Jouishomme, H., et al., *Endocrinology* 130(1):53–60 (1992)). Amino-truncated analogs of PTH-(1–34) also were found to increase PLC activity or $Ca_1^{++}$ in some cells (Donahue, H. J., et al., *J. Biol. Chem.* 263:13522–13527 (1988); Fujimori, A., et al., *Endocrinology* 128(6):3032–3039 (1991); Siegfried, G., et al., *Endocrinology* 136(3): 1267–1275 (1995)) though not in others (Reid, I. R., et al., *Am. J. Physiol.* 253(1 Pt 1):E45–51 (1987); Tamura, T., et al., *Biochem. Biophys., Res. Commun.* 159:1352–1358 (1989)). Studies of the signaling properties of the cloned type I PTHR have focused almost exclusively upon activation of AC, PLC or $Ca_i^{++}$ (Abou-Samra, A. B., et al., *Proc. Natl. Acad. Sci. U.S.A.* 89(7):2732–2736 (1992); Bringhurst, F. R., et al., *Endocrinology* 132(5):2090–2098 (1993); Guo, J., et al., *Endocrinology* 136(9):3884–3891 (1995); Pines, M., et al., *Bone* 18(4):381–389 (1996); Jobert, A.-S., et al., *Endocrinology* 138(12):5282–5292 (1997); Schneider, H., et al., *Eur. J. Pharm.* 246(2):149–155 (1993)), although stimulation of PKC and of PKC-dependent ion transport by hPTH (1–34), hPTH-(3–34) and other hPTH fragments was reported in CHO cells transfected with rat PTHR cDNA (Azarani, A., et al., *J. Biol. Chem.* 271(25):14931–14936 (1996)).

Collectively, these observations have engendered the concept that the structural determinants for activation of AC/PKA signaling are distinct from those required for activation of PLC or PKC and that these reside, respectively, within the N- and C-terminal domains of PTH-(1–34) (Jouishomme, H., et al., *J. Bone Miner. Res.* 9(6):943–949 (1994); Tregear, G. W., and Potts, J. T., Jr. *Endocr. Res. Commun.* 2:561–567 (1975); Whitfield, J. F., and Morley, P. *Trends Pharm. Sci.* 16(11):382–386(1995)). In particular, the region hPTH-(29–32) was identified specifically as a critical PKC activation domain (Jouishomme, H., et al., *J. Bone Miner. Res.* 9(6):943–949 (1994); Whitfield, J. F., and Morley, P. *Trends Pharm. Sci.* 16(11):382–386 (1995)).

Compared with what is known from these studies of the rat PTHR, much less information is available regarding the structural features of human PTH required for binding to the human PTHR or for activation of its various signaling modes. Alanine-scanning mutagenesis has highlighted the importance of the C-terminal portion of hPTH-(1–34) for binding to the rat PTHR (30). Functional studies of transfected human PTHRs in COS-7 or HEK 293 cells have confirmed that hPTH-(1–34) activates AC and $Ca_i^{++}$, although stimulation of PLC was not observed consistently and responses that were reported were modest (Pines, M., et al., *Bone* 18(4):381–389 (1996); Seuwen, K., et al., *Brit. J. Pharm.* 114(8):1613–1620 (1995); Jobert, A.-S., et al., *Endocrinology* 138(12):5282–5292 (1997); Schneider, H., et al., *FEBS Lett.* 351(2):281–285 (1994);). The effects of hPTH-(3–34) on $Ca_i^{++}$ are similarly controversial (Pines, M., et al., *Bone* 18(4):381–389 (1996); Jobert, A.-S., et al., *Endocrinology* 138(12):5282–5292 (1997)), while the roles of other regions of the hPTH-(1–34) molecule in signaling via the human PTHR have not been systematically addressed. Synthetic hPTH-(1–30)$NH_2$, hPTH-(1–29)$NH_2$, hPTH-(1–28)$NH_2$ hPTH-(1–27)$NH_2$, and hPTH-(1–26)$NH_2$ were each incapable of stimulating the activity of membrane-bound PKCs in osteoblast-like ROS17/2 cells (Neugebauer et al. (*Biochem* 34: 8835–8842 (1995)).

SUMMARY OF THE INVENTION

The relatively large size of native PTH presents challenges to the use of these peptides as treatments for osteoporosis. In general, a protein of this size is not suitable for use as a drug, since it cannot be delivered effectively by simple methods such as nasal inhalation. Instead, injection is required, and in the case of PTH, daily, or almost daily injections would most likely be needed to achieve increases in bone formation rates. Additionally, larger peptides are technically difficult and expensive to prepare by conventional synthetic chemistry methods. Alternative methods employing recombinant DNA and cell-based expression systems are also expensive, potentially vulnerable to contamination by foreign proteins and do not circumvent the delivery problem.

Accordingly, it would be advantageous for those skilled in the art to be able to identify a small molecule analog (either peptide or non-peptide) that is based on the larger peptide and yet which still retains the desired biological activities. The activity is greater relative to the intact peptide, but further optimization can lead to enhanced efficacy and potency.

We recently observed that hPTH-(1–31), shown by others to be a full AC agonist but to be incapable of activating PKC via rodent PTHRs (Jouishomme, H., et al., *Endocrinology* 130(1):53–60 (1992)), was as potent as hPTH-(1–34) in activating both AC and PLC via human PTHRs expressed in LLC-PK1, COS-7 or HEK 293 cells (Takasu, H., and Bringhurst, F. R., *Endocrinology* 139(10):4293–4299 (1998)). These unexpected observations prompted us to undertake a more detailed analysis of the relative roles of the extreme N-terminal region of hPTH-(1–34) in binding to, and selective activation of the human PTH-1/PTH-2 receptor, with a particular focus on PLC activation.

The present invention is directed to amino terminal modifications of human parathyroid hormone 1–34 peptide which selectively activate the PTH-2 receptor much more effectively than does the native hPTH(1–34)$NH_2$ ligand but which still activate the classical, PTH-1 receptor, albeit at a reduced level. This unexpected finding has important implications for the design of excellent receptor selective PTH agonists in systems including in vivo where both receptors are expressed. Importantly, the desamino peptides of the present invention are still signal selective via the PTH-1 receptor in that they possess some cAMP activity but minimal PLC activity. Accordingly, the desamino peptides described herein will be useful as bone anabolic agents for the therapeutic treatment of bone disease in vivo.

The present invention relates to PTH(1–34) peptides and derivatives thereof. Compounds of the invention which include PTH(1–34) peptides, fragments thereof, derivatives thereof, pharmaceutically acceptable salts thereof, and N— or C— derivatives thereof, are hereinafter collectively referred to as "compounds of SEQ ID NO:1 and derivatives thereof."

The invention provides synthetic and/or recombinant biologically active peptide derivatives of PTH(1–34). In one specific embodiment, this invention provides a biologically active peptide at least 90% identical to a peptide consisting essentially of the formula:

(a) $X_{01}$ ValSerGluIleGlnLeuMetHisAsnLeuGly LysHisLeuAsnSerMetGluArgValGluTrpLeuArg LysLysLeuGlnAspValHisAsnPhe(SEQ ID NO:1);

(b) fragments thereof containing amino acids 1–29, 1–30, 1–31, 1–32, or 1–33;

(c) pharmaceutically acceptable salts thereof; or (d) N— or C— derivatives thereof, wherein:

$X_{01}$ is desamino Ser, desamino Ala or desamino Gly, provided that said peptide is not desamino $Ser^1$ hPTH(1–31)$NH_2$ or desamino $Ser^1$ hPTH(1–34)$NH_2$.

In accordance with yet a further aspect, this invention also provides pharmaceutical compositions comprising a biologically active peptide at least 90% identical to a peptide consisting essentially of the formula:

(a) $X_{01}$ ValSerGluIleGlnLeuMetHisAsnLeuGly LysHisLeuAsnSerMetGluArgValGluTrpLeuArgLys LysLeuGlnAspValHisAsnPhe(SEQ ID NO:1);

(b) fragments thereof containing amino acids 1–29, 1–30, 1–31, 1–32, or 1–33;

(c) pharmaceutically acceptable salts thereof; or (d) N— or C— derivatives thereof;

wherein:

$X_{01}$ is desamino Ser, desamino Ala or desamino Gly;
and a pharmaceutically acceptable carrier.

In accordance with yet a further aspect, this invention provides a nucleic acid molecule consisting essentially of a polynucleotide encoding a biologically active peptide which has an amino acid sequence selected from the group consisting of:

(a) $X_{01}$ ValSerGluIleGlnLeuMetHisAsnLeuGly
LysHisLeuAsnSerMetGluArgValGluTrpLeuArg
LysLysLeuGlnAspValHisAsnPhe (SEQ ID NO:1);

(b) fragments thereof containing amino acids 1–29, 1–30, 1–31, 1–32, or 1–33;

wherein:

$X_{01}$ is desamino Ser, desamino Ala or desamino Gly, provided that said peptide is not desamino Ser$^1$ hPTH(1–31)NH$_2$ or desamino Ser$^1$ hPTH(1–34)NH$_2$.

In accordance with yet a further aspect, this invention provides a recombinant DNA molecule comprising: (1) an expression control region, said region in operable linkage with (2) a polynucleotide sequence coding for a biologically active peptide, wherein said peptide is selected from the group consisting of:

(a) $X_{01}$ ValSerGluIleGlnLeuMetHisAsnLeuGly
LysHisLeuAsn SerMetGluArgValGluTrpLeuArg
LysLysLeuGlnAspValHisAsnPhe (SEQ ID NO:1);

(b) fragments thereof containing amino acids 1–29, 1–30, 1–31, 1–32, or 1–33;

wherein:

$X_{01}$ is desamino Ser, desamino Ala or desamino Gly, provided that said peptide is not desamino Ser$^1$ hPTH(1–31)NH$_2$ or desamino Ser$^1$ hPTH(1–34) NH$_2$.

In accordance with yet a further aspect, this invention provides a method for treating mammalian conditions characterized by decreases in bone mass, which method comprises administering to a subject in need thereof an effective bone mass-increasing amount of a biologically active peptide, wherein said peptide comprises an amino acid sequence at least 90% identical to a member selected from the group consisting essentially of:

(a) $X_{01}$ ValSerGluIleGlnLeuMetHisAsnLeuGly
LysHisLeuAsnSerMetGluArgValGluTrpLeuArg
LysLysLeuGlnAspValHisAsnPhe (SEQ ID NO:1);

(b) fragments thereof containing amino acids 1–29, 1–30, 1–31, 1–32, or 1–33;

(c) pharmaceutically acceptable salts thereof; or (d) N— or C— derivatives thereof;

wherein:

$X_{01}$ is desamino Ser, desamino Ala or desamino Gly, provided that said peptide is not desamino Ser$^1$ hPTH(1–31)NH$_2$ or desamino Ser$^1$ hPTH(1–34)NH$_2$; and a pharmaceutically acceptable carrier.

In accordance with yet a further aspect, there is provided a method for treating a medical disorder that results from altered or excessive action of the PTH-2 receptor, comprising administering to a patient a therapeutically effective amount of a biologically active peptide wherein said peptide comprises an amino acid sequence at least 90% identical to a member selected from the group consisting essentially of:

(a) $X_{01}$ ValSerGluIleGlnLeuMetHisAsnLeuGly
LysHisLeuAsnSerMetGluArgValGluTrpLeuArg
LysLysLeuGlnAspValHisAsnPhe (SEQ ID NO:1);

(b) fragments thereof containing amino acids 1–29, 1–30, 1–31, 1–32, or 1–33;

(c) pharmaceutically acceptable salts thereof, or (d) N— or C— derivatives thereof;

wherein:

$X_{01}$ is desamino Ser, desamino Ala or desamino Gly, provided that said peptide is not desamino Ser$^1$ hPTH(1–31)NH$_2$ or desamino Ser$^1$ hPTH(1–34)NH$_2$; and a pharmaceutically acceptable carrier sufficient to activate the PTH-2 receptor but not the PTH-1 of said patient.

In accordance with yet a further aspect, this invention also provides a method for determining rates of bone reformation, bone resorption and/or bone remodeling comprising administering to a patient an effective amount of a labeled peptide of SEQ ID NO: 1 or a derivative thereof and determining the uptake of said peptide into the bone of said patient. The peptide may be labeled with a label selected from the group consisting of: radiolabel, flourescent label, bioluminescent label, or chemiluminescent label. An example of a suitable radiolabel is $^{99m}$Tc.

In accordance with yet a further aspect of the invention, any amino-acid substitutions at positions 1–34, and more particularly those amino acid substitutions at amino acid position 1, which do not destroy the biological activity of the PTH(1–34) peptide analog to selectively agonize the PTH-1/PTH-2 receptor (as determined by assays known to the skilled artisan and discussed below), are also included within the scope of the present invention.

DETAILED DESCRIPTION OF THE PREFERRED EMBODIMENTS

Definitions

Figure 1:
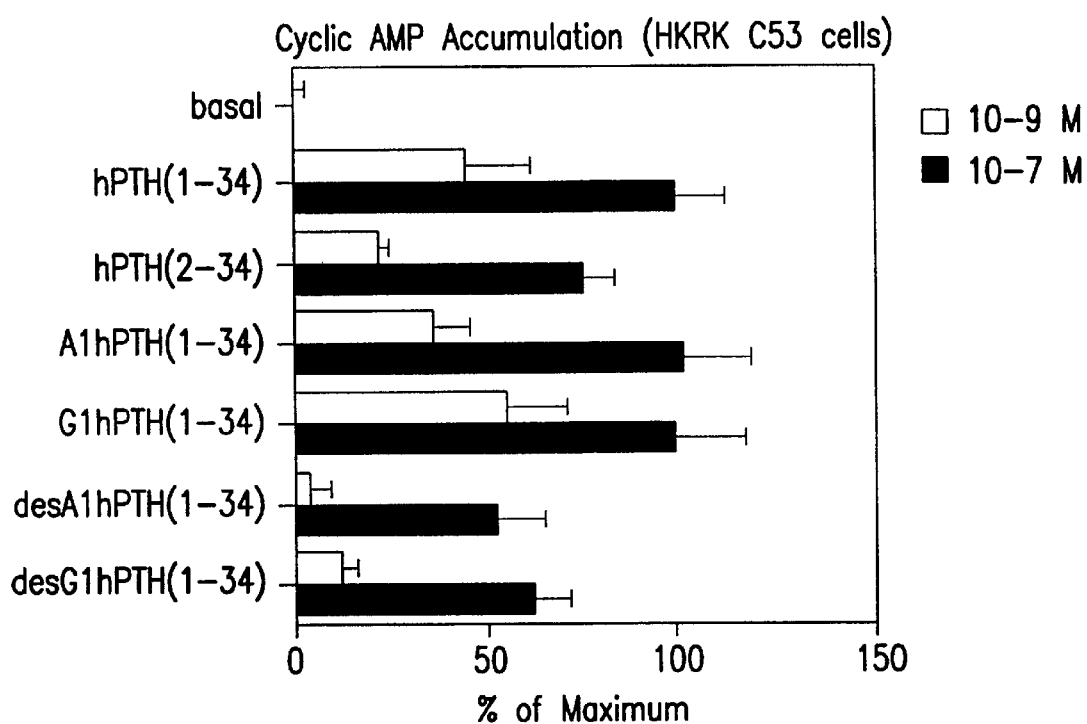
FIG. 1 Measurements of cyclic AMP accumulation in HKRK C53 cells. These are LLC-PK$_1$ porcine renal cells, which stably express approximately 150,000 recombinant hPTH-1 receptors per cell. Data are presented for two concentrations of peptide ($10^{-9}$M (□) and $10^{-7}$M (■)). It can be seen that the Ala$^1$- and Gly$^1$-substituted hPTH(1–34)NH$_2$ molecules have nearly the same efficacy in this assay as does native hPTH(1–34)NH$_2$, whereas their desamino counterparts have greatly reduced activity, particularly noticeable at the 1 nM concentration. The peptide hPTH (2–34) has similarly reduced activity via the PTH-1 receptor.

In the description that follows, a number of terms used in recombinant DNA technology and peptide synthesis are utilized extensively. In order to provide a clear and consistent understanding of the specification and claims, including the scope to be given such terms, the following definitions are provided.

Cloning Vector: A plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

Expression Vector: A vector similar to a cloning vector but which is capable of enhancing the expression of a gene which has been cloned into it, after transformation into a host. The cloned gene is usually placed under the control of (i.e., operably linked to) certain control sequences such as promoter sequences. Promoter sequences may be either constitutive or inducible.

Recombinant Host: According to the invention, a recombinant host may be any prokaryotic or eukaryotic host cell which contains the desired cloned genes on an expression vector or cloning vector. This term is also meant to include those prokaryotic or eukaryotic cells that have been genetically engineered to contain the desired gene(s) in the chromosome or genome of that organism. For examples of such hosts, see Sambrook et al., *Molecular Cloning: A Laboratory Manual*, Second Edition, Cold Spring Harbor Laboratory, Cold Spring Harbor, New York (1989). Preferred recombinant hosts are eukaryotic cells transformed with the DNA construct of the invention. More specifically, mammalian cells are preferred.

Promoter: A DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter. Examples of promoters include the CMV promoter (InVitrogen, San Diego, Calif.), the SV40, MMTV, and hMTIIa promoters (U.S. Pat. No. 5,457,034), the HSV-1 4/5 promoter (U.S. Pat. No. 5,501,979), and the early intermediate HCMV promoter (WO92/17581). Also, tissue-specific enhancer elements may be employed. Additionally, such promoters may include tissue and cell-specific promoters of an organsim.

Polynucleotide: This term generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications have been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

Polypeptide: This term refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in the research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. See, for instance, *Proteins-Structure and Molecular Properties*, 2nd Ed., T. E. Creighton, W. H. Freeman and Company, New York, 1993 and Wold, F., Posttranslational Protein Modifications: Perspectives and Prospects, pgs. 1–12 in *Posttranslational Covalent Modification of Proteins*, B. C. Johnson, Ed., Academic Press, New York, 1983; Seifter et al., "Analysis for protein modifications and nonprotein cofactors", *Methods in Enzymol.* 182:626–646 (1990) and Rattan et al., "Protein Synthesis: Posttranslational Modifications and Aging", *Ann NY Acad Sci* 663:48–62 (1992).

Homologous/Nonhomologous: Two nucleic acid molecules are considered to be "homologous" if their nucleotide sequences share a similarity of greater than 40%, as determined by HASH-coding algorithms (Wilber, W. J. and Lipman, D. J., *Proc. Natl. Acad. Sci*. 80:726–730 (1983)). Two nucleic acid molecules are considered to be "nonhomologous" if their nucleotide sequences share a similarity of less than 40%.

Isolated: A term meaning altered "by the hand of man" from the natural state. If a composition or substance occurs in nature, the isolated form has been changed or removed from its original environment, or both. For example, a polynucleotide or a polypeptide naturally present in a living animal is not "isolated," but the same polynucleotide or polypeptide separated from the coexisting materials of its natural state is "isolated," as the term is employed herein. Thus, a polypeptide or polynucleotide produced and/or contained within a recombinant host cell is considered isolated for purposes of the present invention. Also intended as an "isolated polypeptide" or an "isolated polynucleotide" are polypeptides or polynucleotides that have been purified, partially or substantially, from a recombinant host cell or from a native source. For example, a recombinantly produced version of compounds of SEQ ID NO:1 and derivatives thereof can be substantially purified by the one-step method described in Smith and Johnson, *Gene* 67:31–40 (1988).

Identity: This term refers to a measure of the identity of nucleotide sequences or amino acid sequences. In general, the sequences are aligned so that the highest order match is obtained. "Identity" per se has an art-recognized meaning and can be calculated using published techniques. (See, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H. & Lipton, D., *SIAM J Applied Math* 48:1073 (1988)). Methods commonly employed to determine identity or similarity between two sequences include, but are not limited to, those disclosed in Guide to Huge Computers, Martin J. Bishop, ed., Academic Press, San Diego, 1994, and Carillo, H. & Lipton, D., *SIAM J Applied Math* 48:1073 (1988). Methods to determine identity and similarity are codified in computer programs. Preferred computer program methods to determine identity and similarity between two sequences include, but are not limited to, GCG program package (Devereux, J., et al., *Nucleic Acids Research* 12(i):387 (1984)), BLASTP, BLASTN, FASTA (Atschul, S. F., et al., *J Molec Biol* 215:403 (1990)).

Fragment: A "fragment" of a molecule such as a compound of SEQ ID NO: 1 or derivative thereof is meant to refer to any polypeptide subset of these molecules.

Functional Derivative: The term "derivatives" is intended to include "variants," the "derivatives," or "chemical derivatives" of the molecule. A "variant" of a molecule such as a compound of SEQ ID NO: 1 or derivative thereof is meant to refer to a molecule substantially similar to either the entire molecule, or a fragment thereof. An "analog" of a molecule such as a compound of SEQ ID NO: 1 or derivative thereof is meant to refer to a non-natural molecule substantially similar to either the SEQ ID NO: 1 molecules or fragments thereof.

A molecule is said to be "substantially similar" to another molecule if the sequence of amino acids in both molecules is substantially the same, and if both molecules possess a similar biological activity. Thus, provided that two molecules possess a similar activity, they are considered variants, derivatives, or analogs as that term is used herein even if one of the molecules contains additional amino acid residues not found in the other, or if the sequence of amino acid residues is not identical.

As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Examples of moieties capable of mediating such effects are disclosed in *Remington's Pharmaceutical Sciences* (1980) and will be apparent to those of ordinary skill in the art.

Biological Activity of the Protein: This expression refers to the metabolic or physiologic function of compounds of SEQ ID NO: 1 or derivatives thereof including similar activities or improved activities or those activities with decreased undesirable side-effects. Also included are antigenic and immunogenic activities of said compounds of SEQ ID NO: 1 or derivatives thereof.

Gene Therapy: A means of therapy directed to altering the normal pattern of gene expression of an organism. Generally, a recombinant polynucleotide is introduced into cells or tissues of the organism to effect a change in gene expression.

Host Animal: Transgenic animals, all of whose germ and somatic cells contain the DNA construct of the invention. Such transgenic animals are in general vertebrates. Preferred host animals are mammals such as non-human primates, mice, sheep, pigs, cattle, goats, guinea pigs, rodents, e.g. rats, and the like. The term Host Animal also includes animals in all stages of development, including embryonic and fetal stages.

I. Compounds of SEQ ID NO: 1 and Derivatives Thereof—Structural and Functional Properties The significance of this invention relates to the existence of two cloned species of parathyroid hormone receptors, PTH-1 and PTH-2. These two receptors share significant (greater than 50%) sequence homology and clearly are members of a common receptor family. They appear to be expressed in very different tissues, however. Specifically, the PTH-2 receptor is expressed in certain regions of the brain, lung, endothelium and pancreas, among others, whereas the type 1 receptor is more ubiquitously expressed, especially in kidney and bone. Until now, it has been known only that the PTH-2 receptor was selective for PTH, in that native PTH-related peptide (PTHrP) neither binds to nor activates this receptor. The PTH-2 receptor has been expressed at high levels in homologous cell systems such as HEK kidney cells and shown to signal both adenylyl cyclase and cytosolic free calcium transients.

The discovery has been made that certain amino-terminally modified analogs of hPTH(1–34)NH$_2$, specifically desamino-[Gly¹]hPTH(1–34)NH$_2$ and desamino-[Ala¹]hPTH(1–34)NH$_2$, activate the PTH-2 receptor much more effectively than does the native hPTH(1–34)NH$_2$ ligand. At the same time, these two peptides activate the classical, PTH-1 receptor albeit at a reduced level. The immediate implication of this discovery is that these amino-modified PTH analogs are selective agonists for the PTH-2 receptor.

The present invention relates to hPTH(1–34) peptides and derivatives thereof. Compounds of the invention which include hPTH(1–34) peptides, fragments thereof, derivatives thereof, pharmaceutically acceptable salts thereof, and N— or C— derivatives thereof, are hereinafter collectively referred to as "compounds of SEQ ID NO:1 and derivatives thereof."

In detail, the invention provides synthetic and/or recombinant biologically active peptide derivatives of hPTH (1–34). In one specific embodiment, this invention provides a biologically active peptide at least 90% identical to a peptide consisting essentially of the formula:

(a) X$_{01}$ ValSerGluIleGlnLeuMetHisAsnLeuGly LysHisLeuAsnSerMet GluArgValGluTrpLeuArgLys LysLeuGlnAspValHisAsnPhe(SEQ ID NO:1);

(b) fragments thereof containing amino acids 1–29, 1–30, 1–31, 1–32, or 1–33;

(c) pharmaceutically acceptable salts thereof; or (d) N— or C— derivatives thereof;

wherein:

X$_{01}$ is desamino Ser, desamino Ala or desamino Gly, provided that said peptide is not desamino Ser¹ hPTH(1–31) NH$_2$ or desamino Ser¹ hPTH(1–34)NH$_2$ (SEQ ID NO:8).

The present invention thus provides a novel hPTH (1–34) derivative that is a potent selective PTH-2 receptor agonist. In a preferred embodiment, the hPTH (1–34) derivative is altered at residue 1. Most preferably, the invention includes an hPTH(1–34) derivative having an amino acid substitution of desamino alanine or desamino glycine for serine at position 1 of hPTH (1–34).

In addition, any other amino-acid substitutions of a nature, which do not destroy the ability of the hPTH (1–34) derivative to selectively agonize the PTH-1/PTH-2 receptor (as determined by assays known to the skilled artisan and discussed below), are included in the scope of the present invention.

As protein products, compounds of SEQ ID NO: 1 or derivatives thereof of the present invention are amenable to production by the technique of solution- or solid-phase peptide synthesis. The solid phase peptide synthesis technique, in particular, has been successfully applied in the production of human PTH and can be used for the production of compounds of SEQ ID NO: 1 or derivatives thereof of the present invention (for guidance, see Kimura et al., supra, and see Fairwell et al., *Biochem.* 22:2691 (1983)). Success with producing human PTH on a relatively large scale has been reported by Goud et al., in *J. Bone Min. Res.* 6(8):781 (1991), incorporated herein by reference. The synthetic peptide synthesis approach generally entails the use of automated synthesizers and appropriate resin as solid phase, to which is attached the C-terminal amino acid of the desired compounds of SEQ ID NO: 1 or derivatives thereof. Extension of the peptide in the N-terminal direction is then achieved by successively coupling a suitably protected form of the next desired amino acid, using either FMOC- or BOC-based chemical protocols typically, until synthesis is complete. Protecting groups are then cleaved from the peptide, usually simultaneously with cleavage of peptide from the resin, and the peptide is then isolated and purified using conventional techniques, such as by reversed phase HPLC using acetonitrile as solvent and tri-fluoroacetic acid as ion-pairing agent. Such procedures are generally described in numerous publications and reference may be made, for example, to Stewart and Young, "Solid Phase Peptide Synthesis," 2nd Edition, Pierce Chemical Company, Rockford, Ill. (1984). It will be appreciated that the peptide synthesis approach is required for production of SEQ ID NO: 1 and derivatives thereof variants which incorporate amino acids that are not genetically encoded.

In accordance with another aspect of the present invention, substituents may be attached to the free amine of the N-terminal amino acid of compounds of SEQ ID NO: 1 or derivatives thereof by standard methods known in the art. For example, alkyl groups, e.g., C$_{1-12}$ alkyl, may be attached using reductive alkylation. Hydroxyalkyl groups, e.g. C$_{1-12}$ hydroxyalkyl, may also be attached using reductive alkylation wherein the free hydroxy group is protected with a t-butyl ester. Acyl groups, e.g., COE$_1$, may be attached by coupling the free acid, e.g., E$_1$COOH, to the free amino of the N-terminal amino acid. Also contemplated within the scope of this invention are those compounds of SEQ ID NO:1 and derivatives thereof that alter secondary or tertiary structure, or stability of compounds of SEQ ID NO: 1 or derivatives thereof which still retain biological activity. Such derivatives might be achieved through lactam cyclization, disulfide bonds, or other means known to a person of ordinary skill in the art.

Among the most preferred embodiments of the invention are those compounds which may serve as selective agonists of the PTH-1/PTH-2 receptor In particular, preferred embodiments are those compounds where X$_{01}$ is desamino Gly. The amino acid sequence of this preferred embodiment is thus desaminoGlyValSerGluIleGlnLeuMetHisAsnLeu GlyLysHisLeuAsnSerMetGluArgValGluTrpLeuArgLysLys LeuGlnAspValHisAsnPhe (SEQ ID NO: 2) or derivatives thereof. [[desaminoGly¹]hPTH(1–34)].

Another set of the preferred embodiments are those compounds having a one amino acid deletion at the carboxy terminus of SEQ ID NO: 2 where X$_{01}$ is desamino Gly. The amino acid sequence of this preferred embodiment is thus desaminoGlyValSerGluIleGlnLeuMetHisAsnLeuGlyLys HisLeuAsnSerMetGluArgValGluTrpLeuArgLysLysLeuGln AspValHisAsn (SEQ ID NO: 3) or derivatives thereof. [[desaminoGly¹]hPTH(1–33)].

Another set of the preferred embodiments are those compounds having a seven amino acid deletion at the carboxy terminus of SEQ ID NO: 2 where X$_{01}$ is desamino Gly. The amino acid sequence of this preferred embodiment is thus desaminoGlyValSerGluIleGlnLeuMetHisAsnLeu GlyLysHisLeuAsnSerMet GluArgValGluTrpLeuArgLys Lys (SEQ ID NO: 4) or derivatives thereof. [[desaminoGly¹] hPTH(1–27)].

Another set of the preferred embodiments are those compounds where X$_{01}$ is desamino Ala. The amino acid sequence of this preferred embodiment is thus desaminoA-laValSerGluIleGlnLeuMetHisAsnLeuGlyLysHisLeu AsnSerMetGluArgValGluTrpLeuArgLysLysLeuGln AspValHisAsnPhe (SEQ ID NO: 5) or derivatives thereof. [[desaminoAla¹]hPTH(1–34)].

Another set of the preferred embodiments are those compounds having a one amino acid deletion at the carboxy terminus of SEQ ID NO: 5 where X$_{01}$ is desamino Ala. The amino acid sequence of this preferred embodiment is thus desaminoAlaValSerGluIleGlnLeuMetHisAsnLeuGlyLys HisLeuAsnSerMetGluArgValGluTrpLeuArgLysLysLeu GlnAspValHisAsn (SEQ ID NO: 6) or derivatives thereof. [[desaminoAla$^1$]hPTH(1–33)].

Another set of the preferred embodiments are those compounds having a seven amino acid deletion at the carboxy terminus of SEQ ID NO: 5 where $X_{01}$ is desamino Ala. The amino acid sequence of this preferred embodiment is thus desaminoAlaValSerGluIleGlnLeuMetHisAsnLeu GlyLysHisLeuAsnSerMetGluArgValGluTrpLeuArgLysLys (SEQ ID NO: 7) or derivatives thereof. [[desaminoAla$^1$] hPTH(1–27)].

Another set of the preferred embodiments are those compounds having a one amino acid deletion at the carboxy terminus of SEQ ID NO: 8 where $X_{01}$ is desamino Ser. The amino acid sequence of this preferred embodiment is thus desaminoSerValSerGluIleGlnLeuMetHisAsnLeuGlyLysHis LeuAsnSerMetGluArgValGluTrpLeuArgLysLysLeuGln AspValHisAsn (SEQ ID NO: 9) or derivatives thereof. [[desaminoSer$^1$]hPTH(1–33)].

Another set of the preferred embodiments are those compounds having a seven amino acid deletion at the carboxy terminus of SEQ ID NO: 8 where $X_{01}$ is desamino Ser. The amino acid sequence of this preferred embodiment is thus desaminoSerValSerGluIleGlnLeuMetHisAsnLeu GlyLysHisLeuAsnSerMet GluArgValGluTrpLeuArgLysLys (SEQ ID NO: 10) or derivatives thereof. [[desaminoSer$^1$] hPTH(1–27)].

III. Vectors, Host Cells, and Recombinant Expression

The present invention also relates to vectors that comprise a polynucleotide of the present invention, and host cells which are genetically engineered with vectors of the invention and the production of polypeptides of the invention by recombinant techniques. Cell-free translation systems can also be employed to produce such proteins using RNAs derived from the DNA constructs of present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as *streptococci, staphylococci, E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., Molecular Cloning: A Laboratory Manual (supra).

RNA vectors may also be utilized for the expression of the nucleic acids encoding compounds of SEQ ID NO: 1 or derivatives thereof disclosed in this invention. These vectors are based on positive or negative strand RNA viruses that naturally replicate in a wide variety of eukaryotic cells (Bredenbeek, P. J. & Rice, C. M., *Virology* 3: 297–310, 1992). Unlike retroviruses, these viruses lack an intermediate DNA life-cycle phase, existing entirely in RNA form. For example, alpha viruses are used as expression vectors for foreign proteins because they can be utilized in a broad range of host cells and provide a high level of expression; examples of viruses of this type include the Sindbis virus and Semliki Forest virus (Schlesinger, S., TIBTECH 11:18–22, 1993; Frolov, I., et al., Proc. Natl. Acad. Sci. (USA) 93: 11371–11377, 1996). As exemplified by Invitrogen's Sinbis expression system, the investigator may conveniently maintain the recombinant molecule in DNA form (pSinrep5 plasmid) in the laboratory, but propagation in RNA form is feasible as well. In the host cell used for expression, the vector containing the gene of interest exists completely in RNA form and may be continuously propagated in that state if desired.

For secretion of the translated protein into the lumen of the endoplasmic reticulum, into the periplasmic space or into the extracellular environment appropriate secretion signals may be incorporated into the desired polypeptide. These signals may be endogenous to the polypeptide or they may be heterologous signals.

The expression of a DNA sequence requires that the DNA sequence be "operably linked" to DNA sequences which contain transcriptional and translational regulatory information. An operable linkage is a linkage in which the control or regulatory DNA sequences and the DNA sequence sought to be expressed are connected in such a way as to permit gene expression. The precise nature of the "control regions" needed for gene expression may vary from organism to organism, but shall in general include a promoter region which, in prokaryotic cells, contains both the promoter (which directs the initiation of RNA transcription) as well as DNA sequences which, when transcribed into RNA, will signal the initiation of protein synthesis. Regulatory regions in eukaryotic cells will in general include a promoter region sufficient to direct the initiation of RNA synthesis.

Two DNA sequences are said to be operably linked if the nature of the linkage between the two DNA sequences does not (1) result in the introduction of a frameshift mutation, (2) interfere with the ability of the promoter region sequence to direct the transcription of the fusion protein-encoding sequence or (3) interfere with the ability of the fusion protein-encoding sequence to be transcribed by the promoter region sequence. Thus, a promoter region would be operably linked to a DNA sequence if the promoter were capable of transcribing that DNA sequence.

The joining of various DNA fragments, to produce the expression vectors of this invention is performed in accordance with conventional techniques, employing blunt-ended or staggered-ended termini for ligation, restriction enzyme digestion to provide appropriate termini, filling in of cohesive ends as appropriate, alkali and phosphatase treatment to avoid undesirable joining, and ligation with appropriate ligases. In the case of a fusion protein, the genetic construct encodes an inducible promoter which is operably linked to the 5' gene sequence of the fusion protein to allow efficient expression of the fusion protein.

To express compounds of SEQ ID NO: 1 or derivatives thereof in a prokaryotic cell (such as, for example, *E. coli, B. subtilis*, Pseudomonas, Streptomyces, etc.), it is necessary to operably link the SEQ ID NO: 1-encoding DNA sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene of pBR322, and the CAT promoter of the chloramphenicol acetyl transferase gene of pBR325, etc. Examples of inducible prokaryotic promoters-.include the major right and left promoters of bacteriophage λ, (PL and PR); the trp, recA. lacZ. lacI. and gal promoters of *E. coli*, the α-amylase (Ulmanen, I. et al., *J. Bacteriol.* 162:176–182 (1985)), and the σ-28-specific promoters of *B. subtilis* (Gilman, M. Z. et al., *Gene* 32:11–20 (1984)), the promoters of the bacteriophages of Bacillus (Gryczan, T. J., *In. The Molecular Biology of the Bacilli*, Academic Press, Inc., N.Y. (1982)), and Streptomyces promoters (Ward, J. M. et al., *Mol. Gen. Genet.* 203:468–478 (1986)). Prokaryotic promoters are reviewed by Glick, B. R., *J. Ind. Microbiol.* 1:277–282 (1987); Cenatiempo, Y., *Biochimie* 68:505–516 (1986)); and Gottesman, S., *Ann. Rev. Genet.* 18:415–442 (1984)).

If expression is desired in a eukaryotic cell, such as yeast, fungi, mammalian cells, or plant cells, then it is necessary to employ a promoter capable of directing transcription in such a eukaryotic host. Preferred eukaryotic promoters include the promoter of the mouse metallothionein I gene (Hamer, D. et al., *J. Mol. Appl. Gen.* 1:273–288 (1982)); the TK promoter of Herpes virus (McKnight, S., *Cell* 31:355–365, (1982)); the SV40 early promoter (Benoist, C., et al., *Nature (London)* 290:304–310 (1981)); and the yeast gal4 gene promoter (Johnston, S. A., et al., *Proc. Natl. Acad. Sci. (USA)* 79:6971–6975 (1982); Silver, P. A., et al., *Proc. Natl. Acad. Sci. (USA)* 81:5951–5955 (1984)).

Preferably, the introduced DNA sequence will be incorporated into a plasmid or viral vector capable of autonomous replication in the recipient host. Any of a wide variety of vectors may employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include, without limitation, plasmids such as those capable of replication in *E. coli* (such as, for example, pBR322, ColEl, pSC101, pACYC 184, πVX. Such plasmids are, for example, disclosed by Maniatis, T., et al., In: *Molecular Cloning, A Laboratory Manual*, Cold Spring Harbor Press, Cold Spring Harbor, N.Y. (1982)). Preferred plasmid expression vectors include the pGFP-1 plasmid described in Gardella et al., *J. Biol. Chem.* 265:15854–15859 (1989), or a modified plasmid based upon one of the pET vectors described by Studier and Dunn, *Methods in Enzymology* 185: 60–89 (1990). Bacillus plasmids include pC194, pC221, pT127, etc. Such plasmids are disclosed by Gryczan, T. In: The Molecular Biology of the Bacilli, Academic Press, N.Y. pp. 307–329 (1982). Suitable Streptomyces plasmids include pIJIOI (Kendall, K. J. et al., *J. Bacteriol.* 169:4177–4183 (1987)), and streptomyces bacteriophages such as φC31 (Chater, K. F. et al., *In. Sixth International Symposium on Actinomycetales Biology*, Akademiai Kaido, Budapest, Hungary, pp.45–54 (1986)). Pseudomonas plasmids are reviewed by John, J. F. et al., *Rev. Infect. Dis.* 8:693–704 (1986)), and Izaki, K., *Jon. J. Bacteriol.* 33:729–742 (1978)).

Preferred eukaryotic expression vectors include, without limitation, BPV, vaccinia, 2-micron circle, etc. Such expression vectors are well known in the art (Botstein, D., et al., *Miami Wntr. Symp.* 19:265–274 (1982); Broach, J. R., *In: The Molecular Biology of the Yeast Saccharomyces: Life Cycle and Inheritance*, Cold Spring Harbor Laboratory, Cold Spring Harbor, N.Y. pp. 445–470 (1981); Broach, J. R., *Cell* 28:203–204 (1982); Bollon, D. P., et al., *J. Clin. Hematol. Oncol.* 10:39–48 (1980); Maniatis, T., *In. Cell Biology: A Comprehensive Treatise*, Vol. 3, Gene Expression, Academic Press, N.Y., pp. 563–608 (1980)).

In addition to microorganisms, cultures of cells derived from multicellular organisms may also be used as hosts. In principle, any such cell culture is workable, whether from vertebrate or invertebrate cellular sources. Interest, however, has been greater with cells from vertebrate sources. Examples of useful vertebrate host cell lines are VERO and HeLa cells, Chinese hamster ovary (CHO) cell lines, WI38, BHK, COS-7, and MDCK cell lines. Expression vectors for such cells ordinarily include (if necessary) an origin of replication, a promoter located in front of or upstream to the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, Simian Virus 40 (SV40) and cytomegalovirus. The early and late promoters of SV40 virus are particularly useful because both are obtained easily from the virus as a fragment which also contains the SV40 viral origin of replication (Fiers et al., *Nature* 273:113 (1978)).

An origin of replication may be provided either by construction of the vector to include an exogenous origin, such as may be derived from SV40 or other viral (e.g. Polyoma, Adeno, VSV, BPV) source or may be provided by the host cell chromosomal replication mechanism. If the vector is integrated into the host cell chromosome, the latter is often sufficient.

If cells without formidable cell membrane barriers are used as host cells, transfection is carried out by the calcium phosphate precipitation method as described by Graham and Van der Erb, *Virology* 52:546 (1978). However, other methods for introducing DNA into cells, such as by nuclear injection or by protoplast fusion may also be used. In the case of gene therapy, the direct naked plasmid or viral DNA injection method, with or without transfection-facilitating agents such as, without limitation, liposomes, provides an alternative approach to the current methods of in vivo or in vitro transfection of mammalian cells. If prokaryotic cells or cells which contain substantial cell wall constructions are used, the preferred method of transfection is calcium treatment, using calcium chloride as described in Cohen et al., *Proc. Natl. Acad. Sci. USA* 69:2110 (1972).

IV. Administration and Therapeutic Utility of Compounds of SEQ ID NO:1 or Derivatives Thereof (A) Administration of Compounds of SEQ ID NO:1 or Derivatives Thereof In general, compounds of SEQ ID NO: 1 or derivatives thereof of this invention, or salts thereof, are administered in amounts between about 0.01 and 1 µg/kg body weight per day, preferably from about 0.07 to about 0.2 µg/kg body weight per day. For a 50 kg human female subject, the daily dose of biologically active compounds of SEQ ID NO: 1 or derivatives thereof is from about 0.5 to about 50 µgs, preferably from about 3.5 to about 10 µgs. In other mammals, such as horses, dogs, and cattle, higher doses may be required. This dosage may be delivered in a conventional pharmaceutical composition by a single administration, by multiple applications, or via controlled release, as needed to achieve the most effective results, preferably one or more times daily by injection. Most preferably, this dosage may be delivered in a conventional pharmaceutical composition by nasal insufflation.

The selection of the exact dose and composition and the most appropriate delivery regimen will be influenced by, inter alia, the pharmacological properties of the selected compounds of SEQ ID NO: 1 or derivatives thereof, the nature and severity of the condition being treated, and the physical condition and mental acuity of the recipient.

Representative preferred delivery regimens include, without limitation, oral, parenteral (including subcutaneous, transcutaneous, intramuscular and intravenous), rectal, buccal (including sublingual), transdermal, and intranasal insufflation.

Pharmaceutically acceptable salts retain the desired biological activity of the compounds of SEQ ID NO: 1 or derivatives thereof without toxic side effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalene disulfonic acids, polygalacturonic acid and the like; (b) base addition salts formed with polyvalent metal cations such as zinc, calcium, bismuth, barium, magnesium, aluminum, copper, cobalt, nickel, cadmium, and the like; or with an organic cation formed from N,N'-dibenzylethylenediamine or ethylenediamine; or (c) combinations of (a) and (b), e.g., a zinc tannate salt and the like.

A further aspect of the present invention relates to pharmaceutical compositions comprising as an active ingredient compounds of SEQ ID NO: 1 or derivatives thereof of the present invention, or pharmaceutically acceptable salt thereof, in admixture with a pharmaceutically acceptable, non-toxic carrier. As mentioned above, such compositions may be prepared for parenteral (subcutaneous, transcutaneous, intramuscular or intravenous) administration, particularly in the form of liquid solutions or suspensions; for oral or buccal administration, particularly in the form of tablets or capsules; for rectal, transdermal administration; and for intranasal administration, particularly in the form of powders, nasal drops or aerosols.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985), incorporated herein by reference. Formulations for parenteral administration may contain as excipients sterile water or saline, alkylene glycols such as propylene glycol, polyalkylene glycols such as polyethylene glycol, oils of vegetable origin, hydrogenated naphthalenes and the like. For oral administration, the formulation can be enhanced by the addition of bile salts or acylcarnitines. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

When formulated for the most preferred route of administration, nasal administration, the absorption across the nasal mucous membrane may be enhanced by surfactant acids, such as for example, glycocholic acid, cholic acid, taurocholic acid, ethocholic acid, deoxycholic acid, chenodeoxycholic acid, dehydrocholic acid, glycodeoxycholic acid, cyclodextrins and the like in an amount in the range between about 0.2 and 15 weight percent, preferably between about 0.5 and 4 weight percent, most preferably about 2 weight percent.

Delivery of the compounds of the present invention to the subject over prolonged periods of time, for example, for periods of one week to one year, may be accomplished by a single administration of a controlled release system containing sufficient active ingredient for the desired release period. Various controlled release systems, such as monolithic or reservoir-type microcapsules, depot implants, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

One form of controlled release formulation contains the polypeptide or its salt dispersed or encapsulated in a slowly degrading, non-toxic, non-antigenic polymer such as copoly (lactic/glycolic) acid, as described in the pioneering work of Kent, Lewis, Sanders, and Tice. U.S. Pat. No. 4,675,189, incorporated by reference herein. The compounds or, preferably, their relatively insoluble salts, may also be formulated in cholesterol or other lipid matrix pellets, or silastomer matrix implants. Additional slow release, depot implant or injectable formulations will be apparent to the skilled artisan. See, for example, Sustained and Controlled Release Drug Delivery Systems, J. R. Robinson ed., Marcel Dekker, Inc., New York, 1978, and R. W. Baker, Controlled Release of Biologically Active Agents, John Wiley & Sons, New York, 1987, incorporated by reference herein.

Like PTH, the compounds of SEQ ID NO:1 and derivatives thereof may be administered in combination with other agents useful in treating a given clinical condition. When treating osteoporosis and other bone-related disorders for example, the compounds of SEQ ID NO:1 and derivatives thereof may be administered in conjunction with a dietary calcium supplement or with a vitamin D analog (see U.S. Pat. No. 4,698,328). Alternatively, the compounds of SEQ ID NO:1 and derivatives thereof may be administered, preferably using a cyclic therapeutic regimen, in combination with bisphosphonates, as described for example in U.S. Pat. No. 4,761,406, or in combination with one or more bone therapeutic agents such as, without limitation, calcitonin and estrogen.

(B) Therapeutic Utility of Compounds of SEQ ID NO: 1 or Derivatives Thereof

Compounds of SEQ ID NO: 1 or derivatives thereof of this invention are useful for the prevention and treatment of a variety of mammalian conditions manifested by loss of bone mass. In particular, the compounds of this invention are indicated for the prophylaxis and therapeutic treatment of osteoporosis and osteopenia in humans. Furthermore, the compounds of this invention are indicated for the prophylaxis and therapeutic treatment of other bone diseases. The compounds of this invention are indicated for the prophylaxis and therapeutic treatment of hypoparathyroidism. Finally, the compounds of this invention are indicated for use as agonists for fracture repair and as antagonists for hypercalcemia.

Some forms of hypercalcemia and hypocalcemia are related to the interaction between PTH and PTHrP and the PTH-1 and PTH-2 receptors. Hypercalcemia is a condition in which there is an abnormal elevation in serum calcium level; it is often associated with other diseases, including hyperparathyroidism, osteoporosis, carcinomas of the breast, lung and prostate, epidermoid cancers of the head and neck and of the esophagus, multiple myeloma, and hypernephroma. Hypocalcemia, a condition in which the serum calcium level is abnormally low, may result from a deficiency of effective PTH, e.g., following thyroid surgery.

Nucleic acids of the invention which encode compounds of SEQ ID NO: 1 or derivatives thereof may also be linked to a selected tissue-specific promoter and/or enhancer and the resultant hybrid gene introduced, by standard methods (e.g., as described by Leder et al., U.S. Pat. No. 4,736,866, herein incorporated by reference), into an animal embryo at an early developmental stage (e.g., the fertilized oocyte stage), to produce a transgenic animal which expresses elevated levels of compounds of SEQ ID NO: 1 or derivatives thereof in selected tissues (e.g., the osteocalcin promoter for bone). Such promoters are used to direct tissue-specific expression of compounds of SEQ ID NO: 1 or derivatives thereof in the transgenic animal.

In addition, any other amino-acid substitutions of a nature, which do not destroy the ability of the PTH analog to agonize the PTH-1/PTH-2 receptor (as determined by assays known to the skilled artisan and discussed below), are included in the scope of the present invention.

By "agonist" is intended a ligand capable of enhancing or potentiating a cellular response mediated by the PTH-1/PTH-2 receptor. Whether any candidate "agonist" of the present invention can enhance or inhibit such a cellular response can be determined using art-known protein ligand/receptor cellular response or binding assays, including those described elsewhere in this application.

In accordance with yet a further aspect of the invention, there is provided a method for treating osteoporosis, comprising administering to a patient a therapeutically effective amount of a compound of SEQ ID NO: 1 or a derivative thereof, sufficient to selectively activate the PTH-1/PTH-2 receptor of said patient. To administer the agonist, the appropriate compound of SEQ ID NO: 1 or a derivative thereof is used in the manufacture of a medicament, generally by being formulated in an appropriate carrier or excipient such as, e.g., physiological saline, and preferably administered intravenously, intramuscularly, subcutaneously, orally, or intranasally, at a dosage that provides selective activation of the PTH-1/PTH-2 receptor after binding of a compound of SEQ ID NO: 1 or a derivative thereof. Typical dosage would be 1 ng to 10 mg of the peptide per kg body weight per day. Such dosages and administration may be used for administration of a PTH agonist, e.g., for treatment of conditions such as osteoporosis, other metabolic bone disorders, and hypoparathyroidism and related disorders.

In a preferred embodiment, the compound of SEQ ID NO: 1 or a derivative thereof used in the method has an amino acid substitution of desamino alanine for serine at amino acid position 1 of compound of SEQ ID NO: 1. In this particular embodiment, the PTH derivative is [desamino Ala$^1$]PTH(1–34)(SEQ ID NO: 5). In another preferred embodiment, the compound of SEQ ID NO: 1 or a derivative thereof used in the method has an amino acid substitution of desamino glycine for serine at amino acid position 1 of compound of SEQ ID NO: 1. In this particular embodiment, the PTH derivative is [desaminoGly$^1$] PTH(1–34). (SEQ ID NO: 2).

V. Receptor-Signaling Activities of Compounds of SEQ ID NO: 1 or Derivatives Thereof A crucial step in the expression of hormonal action is the interaction of hormones with receptors on the plasma membrane surface of target cells. The formation of hormone-receptor complexes allows the transduction of extracellular signals into the cell to elicit a variety of biological responses.

A. Screening for PTH-2 Receptor Agonists

Polypeptides of the invention may be screened for their agonistic properties using the cAMP accumulation assay. Cells expressing PTH-2 receptor on the cell surface are incubated with native PTH(1–84) for 5–60 minutes at 37° C., in the presence of 2 mM IBMX (3-isobutyl-1-methylxanthine, Sigma, St. Louis, Mo.). Cyclic AMP accumulation is measured by specific radio-immunoassay, as described above.

A compound of SEQ ID NO: 1 or a derivative thereof that competes with native PTH(1–84) for binding to the PTH-2 receptor, and which stimulates cAMP accumulation in the presence or absence of native PTH(1–84) is a competitive agonist. A compound of SEQ ID NO: 1 or a derivative thereof that does not compete with native PTH(1–84) for binding to the PTH-2 receptor but which is still capable of stimulating cAMP accumulation in the presence or absence of native PTH(1–84), or which stimulates a higher cAMP accumulation than that observed by a compound of SEQ ID NO: 1 or a derivative thereof alone, would be considered a non-competitive agonist.

It will be appreciated to those skilled in the art that the invention can be performed within a wide range of equivalent parameters of composition, concentration, modes of administration, and conditions without departing from the spirit or scope of the invention or any embodiment thereof.

Having now fully described the invention, the same will be more readily understood by reference to specific examples which are provided by way of illustration, and are not intended to-be limiting of the invention, unless herein specified.

EXAMPLE 1

Materials and Methods

Cell Culture

The following cell lines were used in these studies. HKRK C53 subclones of LLC-PKI porcine renal epithelial cells which stably express human PTH-1 receptors (150,000 receptors/cell). SaOS-2 cells are transformed human osteosarcoma cells which express relatively few (10,000–20,000 per cell) human PTH-1 receptors. HPR2–7 cells are subclones of LLC-PK$_1$ which express approximately 250,000 recombinant human PTH-2 receptors per cell. HKRK-B7 cells are subclones of LLC-PK which stably express approximately 1 million hPTH-1 receptors per cell. HPR2-22 cells are subclones of LLC-PK1 which express 1.5 million recombinant hPTH-2 receptors per cell. The HPR2-27 and HPR2-22 cell lines were created in the same fashion as the HKRK cells but employing instead type 2 PTH receptor cDNA using the transfection technique of (Bringhurst, F. R., et al., *Endocrinology* 132(5):2090–2098 (1993); Guo, J., et al., *Endocrinology* 136(9):3884–3891 (1995)).

All cells were maintained under 5% $CO_2$ in air in Dulbecco's modified essential medium containing 7% fetal bovine serum (FBS) and 1% penicillin/streptomycin (GIBCO-BRL, Grand Island, N.Y.). Cells were seeded into 24-well plates two days before assay at a suitable cell density (approximately $2-2.5\times10^5$ cells/well). DNA transfections in COS/HEK cells were performed 24 hr after plating and inositol radiolabel was added 24 hr thereafter (see below). Cell transfections were performed as previously described (Gardella, T. J., et al., *Endocrinology* 132(5):2024–2030 (1993)).

Radioligand Binding and Signaling Assays

Intracellular cAMP accumulation, PLC activation and PTHR binding affinity were measured as previously reported (Bringhurst, F. R., et al., *Endocrinology* 132(5):2090–2098 (1993); Guo, J., et al., *Endocrinology* 136(9):3884–3891 (1995)). Intracellular cAMP accumulation was measured in extracts of cells that were exposed to human PTH peptides in the presence of isobutylmethyxanthine (IBMX, 1 mM) at 37° C. for 15 min. After terminating the reactions by aspiration and freezing in liquid nitrogen, cell monolayers were extracted with 50 mM HCl and cAMP was measured using a radioimmunoassay kit (Dupont-New England Nuclear, Boston, Mass.).

PLC was activated by PTH agonists in the presence of 30 mM LiCl at 37° C. for 30 min after 16 hr of labeling with [$^3$H]myo-inositol (3uCi/ml) in serum-free medium containing 0.1% bovine serum albumin. The reactions were stopped by rapid aspiration and addition of cold 5% TCA. Water-soluble radiolabeled inositol trisphosphate ($IP_3$) was isolated after ether extraction by ion-exchange chromatography (Guo, J., et al., *Endocrinology* 136(9):3884–3891 (1995)). In experiments involving HEK 293 cells, cells previously transfected with human PTHR cDNA (in the pcDNA1 expression vector HKRK) using Lipofectamine (Gibco BRL) were labeled with [$^3$H]myo-inositol and assayed as described above, except that total water-soluble [$^3$H]inositol polyphosphates were collected as a single fraction from the ion-exchange columns.

Radioligand competition binding assays were performed at 2–8° C. for 6 hr using $^{125}$I-[Nle$^{8,21}$]rat PTH-(1–34) (100,000 cpm/well) in the presence or absence of non-radioactive hPTH-(1–34) analogs. Cell layers were washed three times before solubilization for determination of cell-associated radioactivity.

The average levels basally and in the presence of maximal concentrations of hPTH-(1–34) observed in HKRK C53 cells for the assays reported here were 12±4 and 207±37 pmoles/well/15 min for cAMP accumulation, 898±142 and 1908±251 cpm/well for $IP_3$ formation and 25520±1909 and 956±135 cpm/well for binding, respectively. The average levels basally and in the presence of maximal concentrations of hPTH-(1–34) observed in HKRK B28 cells for the assays reported here were 1.6±0.5 and 337±55 pmoles/well/15 min for cAMP accumulation, and 1497±121 and 16,137±919 cpm/well for binding, respectively. The average levels basally and in the presence of maximal concentrations of hPTH-(1–34) observed in HPR2-7 cells for the assays reported here were 2.5±1.0 and 133±14 pmoles/well/15 min for cAMP accumulation, and 1156±243 and 4541±386 cpm/well for binding, respectively. The average levels basally and in the presence of maximal concentrations of hPTH-(1–34) observed in HPR2-22 cells for the assays reported here were 5.2±0.5 and 286±8 pmoles/well/15 min for cAMP accumulation, and 335±68 cpm/well (basal) for $IP_3$ formation, respectively.

Peptides and Other Reagents

All reagents were purchased from Sigma (St. Louis, Mo.), unless otherwise specified. All isotopes were obtained from Dupont New England Nuclear (Boston, Mass.). Human PTH peptides were synthesized in the Biopolymer Core Laboratory of the Endocrine Unit with C-terminal amidation and, when present, substitution of Tyr$^{34}$ for the naturally occurring Phe$^{34}$. [Tyr$^0$]hPTH-(1–34) was purchased from Sigma Co. $^{125}$I-[E Nle$^{8,21}$]rat PTH-(1–34) was iodinated and purified as previously described (Bringhurst, F. R., et al., *Endocrinology* 132(5):2090–2098 (1993); Guo, J., et al., *Endocrinology* 136(9):3884–3891 (1995)).

Results

N-terminally Modified hPTH Analogs

We addressed the role of the N-terminal Ser$^1$ residue and of its (x-amino group in binding to and activation of the human PTH-1 and PTH-2 receptor. Because earlier work with isolated rat renal membranes had shown that substitution of Ala$^1$ for Ser$^1$ in hPTH-(1–34) increased its AC activity, whereas a Gly$^1$ substitution impaired AC activation by bPTH-(1–34) (Tregear, G. W., and Potts, J. T., Jr. *Endocr. Res. Commun.* 2:561–567 (1975)), these position-1 modifications were introduced into hPTH-(1–34) and the resultant peptides were used to compare the effect of the modifications at the N-terminus of hPTH(1–34) on binding to, and activation of, these two receptors expressed in the various cell lines tested. The results for measurements of cyclic AMP accumulation are shown in FIGS. 1–3.

FIG. 1 shows measurements of cyclic AMP accumulation in HKRK C53 cells. There are LLC-$PK_1$ porcine renal cells, which stably express approximately 150,000 recombinant hPTH-1 receptors per cell. Data are presented for two concentrations of peptide ($10^{-9}$M and $10^{-7}$M). It can be seen that the Ala$^1$- and Gly$^1$-substituted hPTH(1–34)$NH_2$ molecules have nearly the same efficacy in this assay as native hPTH(1–34)$NH_2$, whereas their desamino counterparts have greatly reduced activity, particularly noticeable at the 1 nM concentration. The peptide hPTH(2–34) has similarly reduced activity via the PTH-1 receptor.

Figure 2:
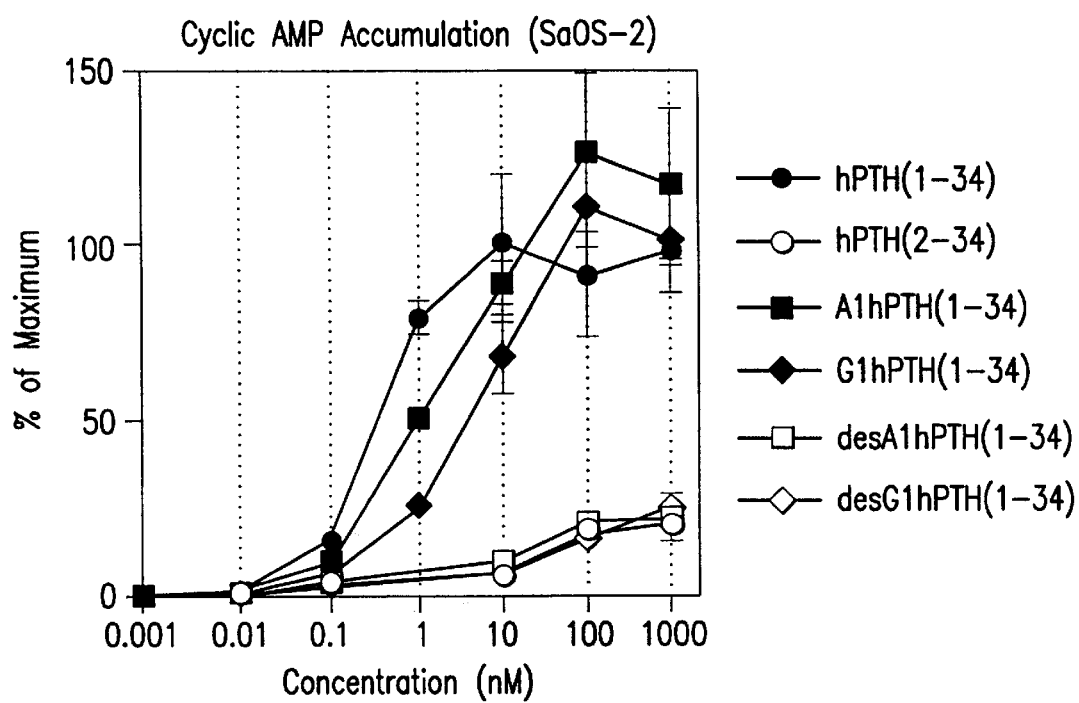
FIG. 2 cAMP measurements in SaOS-2 cells. These are transformed human osteosarcoma cells which are known to express relatively few (10,000–20,000 per cell) human PTH-1 receptors. As shown in the figure, the cyclase activity of the [Gly$^1$] (♦) and [Ala$^1$] hPTH(1–34)NH$_2$ (■) analogs again is comparable to that of the control peptide hPTH (1–34) peptide (●), whereas the desamino-[Ala$^1$] (□) and -[Gly$^1$] (◇) peptides, like the hPTH(2–34) peptide, display minimal activity, even at very high concentrations (i.e., micromolar).

FIG. 2 shows cAMP measurements in SaOS-2 cells. These are transformed human osteosarcoma cells which are known to express relatively few (10,000–20,000 per cell) human PTH-1 receptors. As shown in FIG. 2, the cyclase activity of the [Gly$^1$] and [Ala$^1$] hPTH(1–34)$NH_2$ analogs again is comparable to that of the control peptide hPTH (1–34)$NH_2$, whereas the desamino anologs, like hPTH (2–34), are very weak agonists at the highest concentration tested (1 uM).

Figure 3:
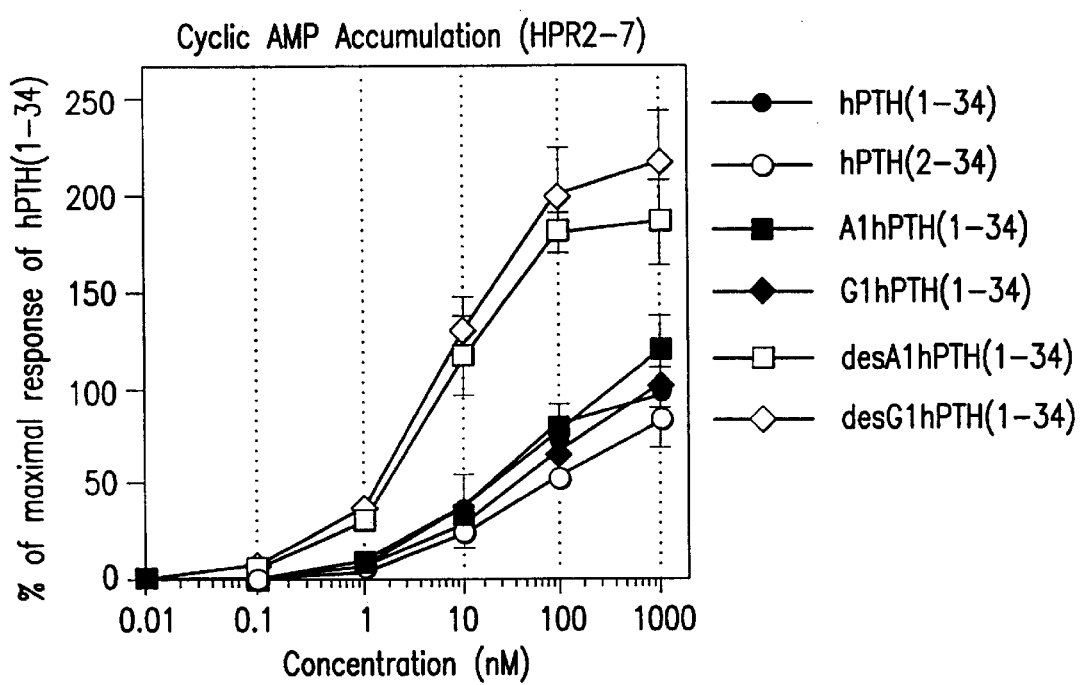
FIG. 3 cAMP measurements in clonal LLC-PK$_1$ cells (HPR2–7). Clonal LLC-PK$_1$ cells (HPR2–7) express approximately 250,000 recombinant human PTH-2 receptors per cell. Desamino-[Ala$^1$] (□) and -[Gly$^1$] (◇) peptides display enhanced efficacy in comparison with hPTH (1–34)NH$_2$ (●), hPTH(2–34) (○) or their [Ala$^1$] (■) and [Gly$^1$] (♦) substituted counterparts. The desamino peptides displayed a substantially greater maximal cyclase activation at very high concentrations (1 micromolar).

In contrast to these observations made in cells that express PTH-1 receptors, FIG. 3 demonstrates the cAMP responsiveness to the same peptides when they are added to other clonal LLC-$PK_1$ cells (HPR2-7) that express approximately 250,000 recombinant human PTH-2 receptors per cell. It is evident from FIG. 3 that the desamino-[Ala$^1$] and -[Gly$^1$] peptides display enhanced efficacy in comparison with hPTH(1–34)$NH_2$, hPTH(2–34) or their [Ala$^1$] and [Gly$^1$] substituted counterparts. In addition, the desamino peptides show a substantially greater maximal cyclase activation at very high concentrations (1 micromolar).

Human PTH-(3–34) had been characterized previously as a PLC/PKC-selective peptide via rodent PTH receptors (Azarani, A., et al., *J. Biol. Chem.* 271(25): 14931–14936 (1996); Fujimori, A., et al., *Endocrinology* 128(6): 3032–3039 (1991); Jouishomme, H., et al., *Endocrinology* 130(1):53–60 (1992)). We have observed, however, that this peptide, at concentrations as high as 1000 nM, did not activate PLC in HKRK B7 cells or in COS-7 cells that expressed rat or human PTHRs (Takasu et al., *J. Bone Miner. Res.*, In Press). These results indicated that the first two amino acids at the N-terminus of hPTH-(1–34) (Ser$^1$-Val$^2$) must be important for PLC as well as AC activation via the human PTHR.

Figure 4:
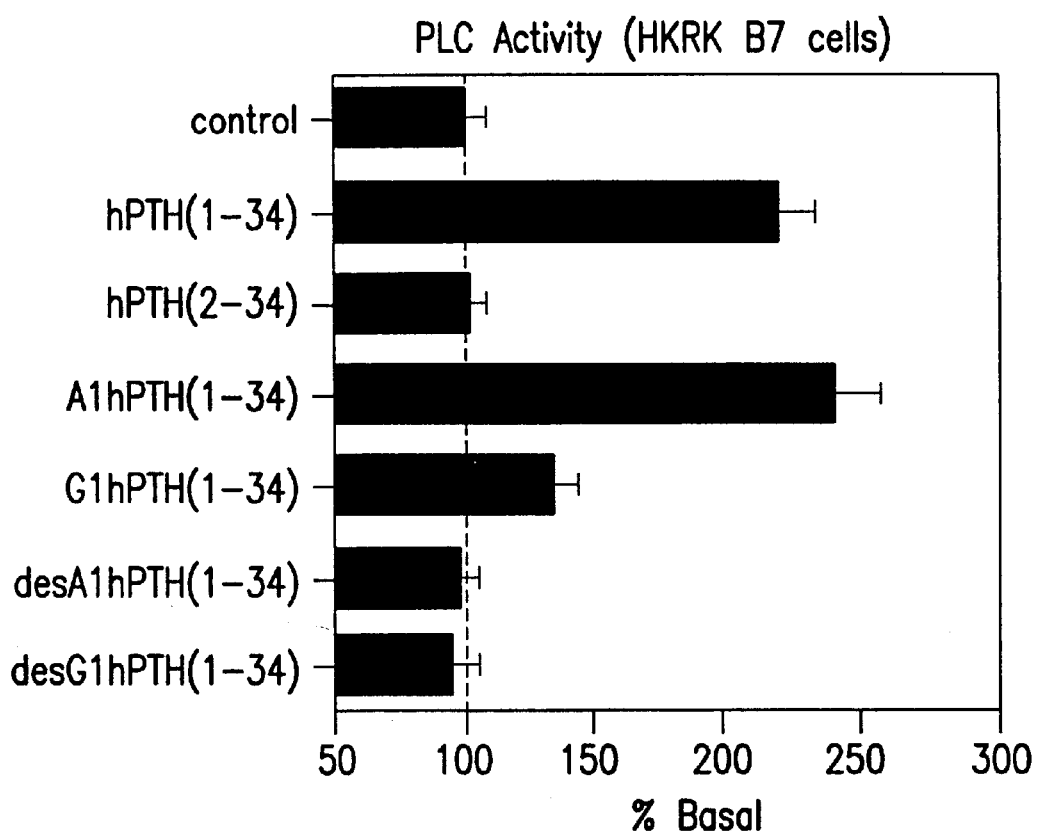
FIG. 4 Measurements of phospholipase C (PLC) activity in LLC-PK cells (HKRK-B7) that stably express approximately 1 million human PTH-1 receptors per cell. Desamino-[Ala$^1$] and -[Gly$^1$] compounds exert no activation of PLC via this receptor, whereas hPTH(1–34)NH$_2$ and [Ala$^1$]hPTH(1–34)NH$_2$ are full agonists. [Gly$^1$]hPTH(1–34) NH$_2$ and hPTH(1–34)NH$_2$ are only partial agonists for PLC activation via the type 1 hPTH receptor). Human PTH (2–34), like the desamino peptides, is inactive in this assay (1000 nM concentration).
Figure 5:
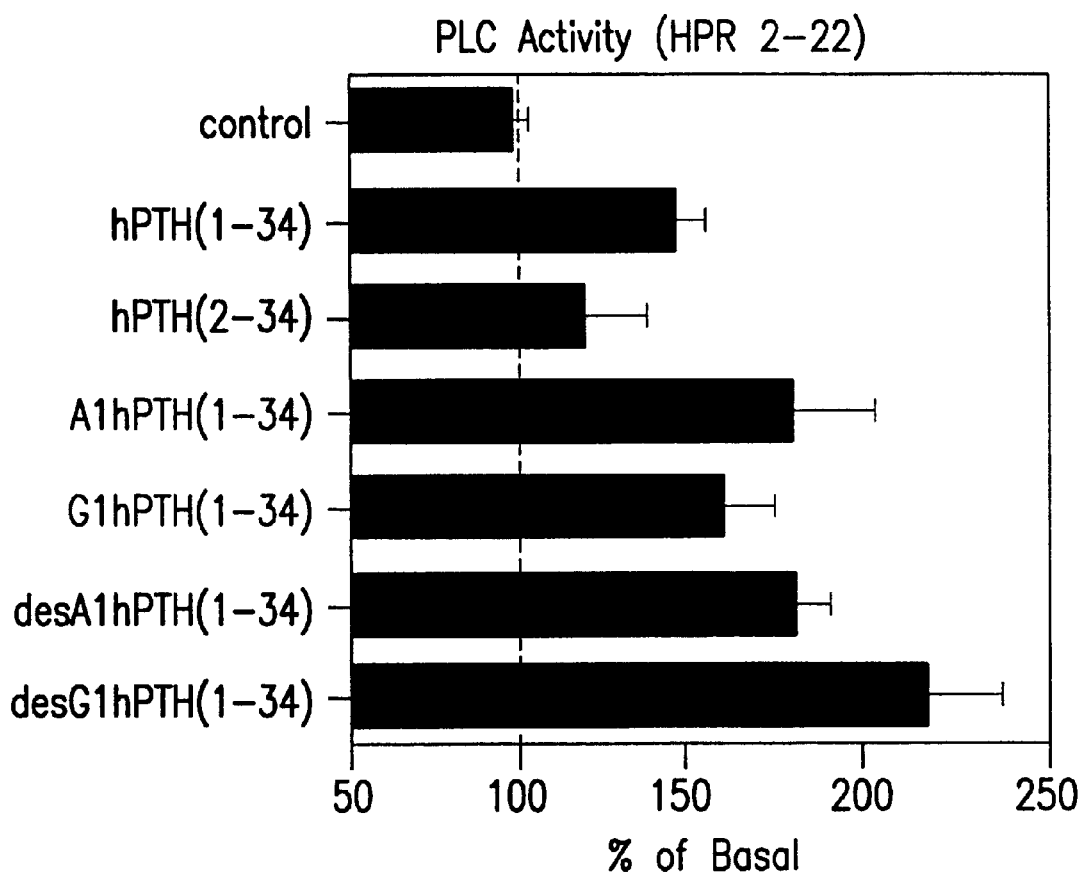
FIG. 5 Phospholipase C activating profiles of these peptides in cells (HPR2–22) that express 1.5 million recombinant human PTH-2 receptors per cell. As seen in the figure, both desamino peptides exert greater maximal activation of phospholipase C at the concentration tested (1,000 nM) than does human PTH(1–34)NH$_2$. Human PTH(2–34), which has activity similar to the desamino peptides via the PTH-1 receptor, is seen to be only a partial agonist in this assay.
Figure 6A:
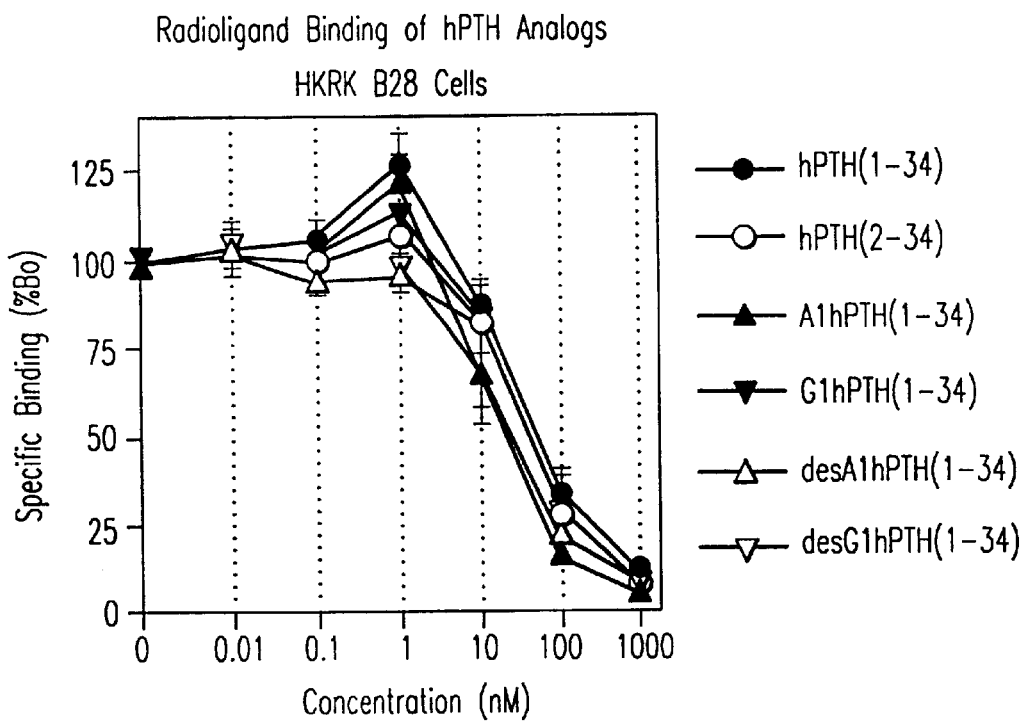
FIG. 6 Radioligand binding of hPTH analogs. The enhanced potency of the desamino peptides for the PTH-2 receptor is associated with a 10-fold higher apparent binding affinity, relative to hPTH(1–34), to that receptor (vs the PTH-1 receptor). As shown in the figure, hPTH(1–34)(●), HPTH(2–34)(0) and the desamino peptides exhibit similar competitive displacement of $^{125}$I-[Nle$^{8,21}$]rPTH(1–34) radioligand binding to HKRK B28 cells that express 280,000 recombinant PTH-1 receptors/cell, whereas the desamino compounds are 10-fold more potent in displacing this radioligand from HPR2–7 cells that express the human PTH-2 receptor.
Figure 6B:
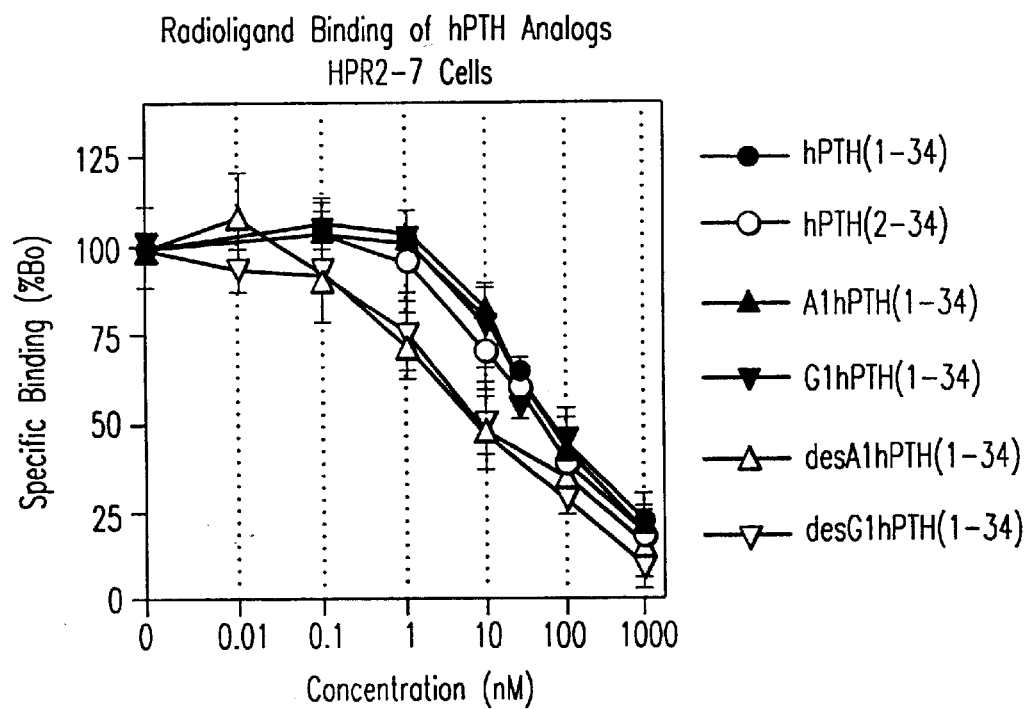

To refine this analysis, we first studied the properties of hPTH-(2–34) in the various cell lines. As shown in FIGS. 4 and 5, hPTH-(2–34) did not elicit PLC activity in HKRK B7 cells, even though its activation of AC was comparable in magnitude and sensitivity to that of hPTH-(1–34). In addition, as shown in FIG. 6, PTH(2–34) also binds as well to the hPTH receptor as does PTH(1–34). Similar results were obtained using COS-7 cells expressing abundant human PTHRs (data not shown). The inability of hPTH-(2–34) to activate PLC via the human PTH-1 receptor was confirmed in a fully homologous system by using HEK-293 human embryonic kidney cells that were transiently transfected with human PTHR cDNA (data not shown).

We next addressed the effect of the extreme N-terminal amino acid of PTH(1–34) on the activation of the PLC/PKC pathway. FIG. 4 shows measurements of phospholipase C (PLC) activity following addition of the indicated peptides at a final concentration of 1000 nM to LLC-PK cells (HKRK-B7) that stably express approximately 1 million hPTH-1 receptors per cell. As shown in FIG. 4, the desamino-[Ala$^1$] and -[Gly$^1$] compounds exert no activation of PLC via this receptor, whereas hPTH(1–34)NH$_2$ and [Ala$^1$hPTH(1–34)NH$_2$ are both fill agonists. The [Gly$^1$] hPTH(1–34)NH$_2$ substituted peptide showed diminished PLC activity (approximately 50% of the hPTH(1–34) maximum) at the concentration tested and is thus only a partial agonist for PLC activation via this receptor. Human PTH(2–34), like the desamino peptides, is inactive in this assay.

Shown in FIG. 5, in contrast, are phospholipase C activating profiles of these peptides in HPR 2–22 cells that express 1.5 million recombinant hPTH-2 receptors per cell. As seen in the figure, both the desamino-[Ala$^1$] and -[Gly$^1$] hPTH(1–34) peptides exert greater maximal activation of phospholipase C at the concentration tested (1,000 nM) than does human PTH(1–34)NH$_2$. Human PTH(2–34), which has activity similar to the desamino peptides via the PTH-1 receptor, is seen to be only a partial agonist in this assay.

As shown in FIG. 6, the enhanced potency of the desamino peptides for the PTH-2 receptor is associated with a 10-fold higher apparent binding affinity, relative to hPTH (1–34), to that receptor (vs the PTH-1 receptor). As shown in the figure, hPTH(1–34), HPTH(2–34) and the desamino peptides exhibit similar competitive displacement of $^{125}$I-Nle$^{8,21}$]rPTH(1–34) radioligand binding to HKRK B28 cells that express 280,000 recombinant human PTH-1 receptors/cell, whereas the desamino compounds are 10-fold more potent in displacing this radioligand from HPR2–7 cells that express the human PTH-2 receptor.

Discussion

The findings presented in these experiments require that some key aspects of current models of the structural determinants of PTH-1 and PTH-2 signaling be re-examined. Work conducted previously with rodent and opossum cells that express endogenous PTHRs had shown that N-truncated PTH analogs, such as PTH-(3–34), lack AC activity but nevertheless can potently activate PKC and, in some systems (Donahue, H. J., et al., *J. Biol. Chem.* 263:13522–13527 (1988); Fujimori, A., et al., *Endocrinology* 128(6):3032–3039 (1991); Siegfried, G., et al., *Endocrinology* 136(3):1267–1275 (1995)), but not others (Reid, I. R., et al., *Am. J. Physiol.* 253(1 Pt 1):E45–51 (1987); Tamura, T., et al., *Biochem. Biophys., Res. Commun.* 159:1352–1358 (1989)), Ca$_i^{++}$ transients. Detailed analysis of the PKC-activating properties of N- and C-truncated hPTH-(1–34) analogs led to the conclusion that the sequence hPTH-(29–32) represents a critical "PKC activation domain" (Jouishomme, H., et al., *J. Bone Miner. Res.* 9(6):943–949 (1994); Jouishomme, H., et al., *Endocrinology* 130(1):53–60 (1992);Whitfield, J. F., and Morley, P. *Trends Pharm. Sci.* 16(11):382–386 (1995)).

In order to determine if the PTH-1 and PTH-2 receptors recognize the same structure features of the PTH ligand, we compared the effect of modifications of the N-terminus of hPTH(1–34) on binding to, and activation of, these two receptors. In comparisons between clonal LLC-PK1 cells that stably expressed human PTH-1 vs. human PTH-2 receptors, hPTH(1–34) elicited concentration dependent activation of AC, with EC50s of 1 nM, respectively. Human PTH(2–34) was less active ($\leq$10 fold) via both receptors. Substitution of Ala or Gly for the N-terminal Ser residue of hPTH(1–34) did not alter AC activation via either receptor when tested in cells expressing either 150,000 (HKRK C53) or 10,000–20,000 (SaOS) human PTH-1 receptors per cell. Removal of the a-amino group to produce desamino-[Ala$^1$] hPTH(1–34) or desamino-[Gly$^1$]hPTH(1–34) reduced AC activity via the human PTH-1 receptor by 10-fold. In striking contrast, we found that these desamino peptides activated the human PTH-2 receptor with greatly enhanced potency: the EC50 for both was 3-fold lower (10 nM vs. 30 nM) and the maximal response twice that seen with hPTH (1–34).

Amino-truncated analogs, including bPTH-(2–34), hPTH-(2–38) and desamino-PTH-(1–34), previously were found to exhibit only weak AC activity when tested in vitro (Fujimori, A., et al., *Endocrinology* 128(6):3032–3039 (1991); Fujimori, A., et al., *Endocrinology* 130(1):29–36 (1992); Tregear, G. W., and Potts, J. T., Jr. *Endocr. Res. Commun.* 2:561–567 (1975); Rixon, R. H., et al., *J. Bone Miner. Res.* 9(8):1179–1189 (1994)), whereas we found that hPTH-(2–34), desamino-[Ala$^1$]hPTH-(1–34) and desamino-[Gly$^1$]hPTH-(1–34) were approximately equipotent with hPTH-(1–34). This disparity in AC activation is likely explained by the much larger number of human PTH-1 receptors expressed by the HKRK B7 cells than by the osteosarcoma cells or partially purified membranes used in previous studies (Fujimori, A., et al, *Endocrinology* 128(6): 3032–3039 (1991); Fujimori, A., et al., *Endocrinology* 130 (1):29–36 (1992); Tregear, G. W., and Potts, J. T., Jr. *Endocr. Res. Commun.* 2:561–567 (1975); Rixon, R. H., et al., *J. Bone Miner. Res.* 9(8):1179–1189 (1994)).

The HKRK B7 cells were also selected for these studies to optimize analysis of the structural basis of PLC signaling via human PTHRs, which requires a high level of receptor expression (Guo, J., et al., *Endocrinology* 136(9):3884–3891 (1995); Pines, M., et al., *Endocrinology* 135(4):1713–1716 (1994)). When these N-truncated peptides were tested with other LLC-PKI subclones that expressed fewer human PTHRs (i.e. 100,000–300,000 per cell), their AC responses were indeed reduced by as much as 10-fold, relative to hPTH-(1–34) (data not shown). On the other hand, studies of such N-truncated PTH analogs in vivo have demonstrated greater biopotency than predicted from measures of AC activity in vitro (Tregear, G. W., et al., *Endocrinology* 93:1349–1353 (1973); Hilliker, S., et al., *Bone* 19:469–477 (1996)). Also, the actual number of PTH-1 receptors expressed by relevant target cells in vivo remains uncertain but could be within the range studied here (Shukunarni, C., et al., *J. Cell Biol.* 133(2):457–468 (1996); Bos, M. P., et al., *Calcif. Tiss. Internat.* 58(2):95–100 (1996)).

Previous studies of the effects of hPTH-(1–34) or PTH-(3–34) on PLC activation or $Ca_i^{++}$ signaling via recombinant human PTHRs expressed heterologously in COS-7 or HEK-293 cells produced discordant findings (Pines, M., et al., *Bone* 18(4):381–389 (1996); Seuwen, K., et al., *Brit. J. Pharm.* 114(8):1613–1620 (1995); Jobert, A.-S., et al., *Endocrinology* 138(12):5282–5292 (1997); Schneider, H., et al., *FEBS Lett.* 351(2):281–285 (1994)). Because of the numerous observations that N-terminally truncated PTH analogs trigger activation of PKC and $Ca_i^{++}$ in other systems (Azarani, A., et al., *J. Biol. Chem.* 271(25):14931–14936 (1996); Donahue, H. J., et al., *J. Biol. Chem.* 263:13522–13527 (1988); Fujimori, A., et al., *Endocrinology* 128(6):3032–3039 (1991); Fujimori, A., et al., *Endocrinology* 130(1):29–36 (1992); Janulis, M., et al., *Endocrinology* 133:713–719 (1993); Jouishomme, H., et al., *Endocrinology* 130(1):53–60 (1992); Chakravarthy, B. R., et al., *Biochem. Biophys. Res. Commun.* 171(3):1105–1110 (1990); Cole, J. A., et al., *Endocrinology* 1229:2981–2989 (1989); Rixon, R. H., et al., *J. Bone Miner. Res.* 9(8):1179–1189 (1994)), however, our finding that a free α-amino group at position-1 of hPTH-(1–34) is an absolute requirement for PLC activation via the human PTH-1 receptor was quite unexpected. In fact, our data indicate that PLC activation via the PTH-1 receptor is even more sensitive to such subtle N-terminal modifications than is AC, and, in contrast to the consequences of stepwise C-terminal truncation of hPTH-(1–34)(data not shown), the reduction in PLC potency of these analogs cannot be attributed to lower binding affinity. This suggests that the extreme N-terminus of hPTH-(1–34) constitutes a true "activation domain" for PLC signaling via the human PTH-1 receptor. We should note that others previously have reported activation of PLC by the N-truncated peptides bPTH-(2–34) and bPTH-(3–34) in rat UMR 106-01 osteosarcoma cells (Fujimori, A., et al., *Endocrinology* 128(6):3032–3039 (1991)). The explanation for this discrepancy could lie in species differences (in cells and ligand) or in the possible expression by UMR osteosarcoma cells of alternate species of PLC-coupled PTH receptors, the presence of which could not be excluded in rat osteosarcoma cells that also expressed endogenous PTH-1 receptors (Murray, T. M., et al., *Calcif. Tiss. Internat.* 49(2):120–123 (1991); Inomata, N., et al., *Endocrinology* 136(11):4732–4740 (1995)). The failure of N-truncated hPTH-(1–34) analogs studied here to activate PLC via cloned human PTH-1 receptors was not unique to the porcine host cells, however, as these findings were confirmed in both COS-7 cells and in a homologous human cell system as well (data not shown).

Several major conclusions regarding the interaction of hPTH-(1–34) and the PTH-1 and PTH-2 receptor can be drawn from the results of these experiments. First, it is clear that an intact N-terminus of the hPTH-(1–34) ligand is indispensable for effective activation of PLC via the PTH-1 receptor. Second, although the N-terminus of hPTH is important for activation of both AC and PLC via the PTH-1 receptor, the roles of specific structural features within the N-terminus of the ligand in activating these two effectors are different. Specifically, we found that PLC activation is much more sensitive to the structure of the N-terminus—i.e. both the identity of the N-terminal amino acid and the presence of the N-terminal α-amino group—than is the AC response, which, unlike PLC, can occur normally even in the absence of an amino acid at position 1. We had previously accomplished such signaling selectivity through mutations in the PTH receptor (by changing the EKKY sequence in intracellular loop 2 to DSEL (Iida-Klein, A., et al., *J. Biol. Chem.* 272(11):6882–6889 (1997)), but it now is clear that a highly signal-selective ligand, active through the wild type receptor, also can be designed.

Furthermore, because the desamino peptides in these studies did not activate PLC via the PTH-1 receptor but stimulated PLC via the PTH-2 receptor to a level 50% greater than the maximal responses observed with 1000 nM hPTH(1–34), we conclude that the human PTH-1 and PTH-2 receptors differ in their recognition of key structural features at the N-terminus of the hPTH ligand. Moreover, the greatly reduced efficacy of hPTH(1–34) for AC activation via PTH-2 vs. PTH-1 receptors in cells with comparable receptor expression, together with the enhanced signaling and binding observed with amino-terminally modified hPTH peptides suggests that PTH may not be the natural ligand for the PTH-2 receptor.

Of course, until physiologic levels of PTH-1/PTH-2 receptor expression have been defined in relevant target cells in vivo, estimates of the AC activity of PTH analogs or mimetic compounds obtained using these highly sensitive in vitro systems must be interpreted cautiously. At the same time, such systems appear to offer important advantages for identifying weak human PTH-1/PTH-2 receptor agonists and defining the elemental structural features of ligands involved in binding and multiple parallel signaling by this receptor.

Careful analysis of the properties of these analogs in vitro and in vivo should help clarify the role of PTH-1/PTH-2 receptor-dependent PLC activation in PTH action(s) and provide further direction for the development of other signal-selective hPTH analogs.

Further clarification of the significance of these various activation domains for physiological or pharmacological actions of PTH in vivo will require better definition of the roles of key cellular pathways activated by PTH-1/PTH-2 receptor-mediated AC, and PLC signaling. These issues now can be addressed more clearly by comparing biological actions of the N-terminally modified PTH analogs described here with those of N-terminally shortened PTH analogs described by others (Azarani, A., et al., *J. Biol. Chem.* 271(25):14931–14936 (1996); Janulis, M., et al., *Endocrinology* 133:713–719 (1993); Siegfried, G., et al., *Endocrinology* 136(3):1267–1275 (1995); Rixon, R. H., et al., *J. Bone Miner. Res.* 9(8):1179–1189 (1994)) that trigger PKC activation but not PLC. For example, we previously found that selective ablation of the PLC response to PTH-(1–34) via mutations within the second intracellular loop of the rat PTHR blocks certain downstream biologic responses, such as sodium-dependent phosphate transport in LLC-PK1 cells (Iida-Klein, A., et al., *J. Biol. Chem.* 272(11):6882–6889 (1997)) and interleukin-6 production by growth-plate chondrocytes (unpublished data). The availability of novel ligands with receptor specific selective signaling via the wild type PTH-1/PTH-2 receptors now offers a complementary approach to addressing important questions in vitro. Ultimately, careful correlation of in vitro tests with studies of analog activity in vivo will be required to dissect and full define the physiological roles of these separate receptor specific signals.

What is claimed is:

1. An isolated biologically active peptide consisting essentially of the formula:
   (a) $X_{01}$ValSerGluIleGlnLeuMetHisAsnLeuGlyLysHisLeuAsnSerMetGluArgValGluTrpLeuArgLysLysLeuGlnAspValHisAsnPhe (SEQ ID NO: 1);
   (b) fragments thereof containing amino acids 1–29, 1–30, 1–31, 1–32, or 1–33;
   (c) pharmaceutically acceptable salts thereof; or
   (d) N— or C— derivatives thereof;
   wherein:
   $X_{01}$ is desamino Ser, desamino Ala or desamino Gly, provided that said peptide is not desamino-SerValSerGluIleGlnLeuMetHisAsnLeuGlyLysHisLeuAsnSerMetGluArgValGluTrpLeuArgLysLysLeuGlnAspValHisAsnPhe (SEQ ID NO:8) or a fragment thereof containing amino acids 1–31.

2. The peptide of claim 1 which is: desamino-AlaValSerGluIleGlnLeuMetHisAsnLeuGlyLysHisLeuAsnSerMetGluArgVal GluTrpLeuArgLysLysLeuGlnAspValHisAsnPhe(SEQ ID NO:5).

3. The peptide of claim 1 which is: desamino-GlyValSerGluIleGlnLeuMetHisAsnLeuGlyLysHisLeuAsnSerMetGluArgVal GluTrpLeuArgLysLysLeuGlnAspValHisAsnPhe(SEQ ID NO:2).

4. The peptide of claim 1 wherein the peptide is labeled with a label selected from the group consisting of: radiolabel, flourescent label, bioluminescent label, or chemiluminescent label.

5. The peptide of claim 4, wherein said radiolabel is $^{99m}$Tc.

6. A pharmaceutical composition comprising an isolated biologically active peptide consisting essentially of the formula:
   (a) $X_{01}$ValSerGluIleGlnLeuMetHisAsnLeuGlyLysHisLeuAsnSerMetGluArgValGluTrpLeuArgLysLysLeuGlnAspValHisAsnPhe(SEQ ID NO:1);
   (b) fragments thereof containing amino acids 1–29, 1–30, 1–31, 1–32, or 1–33;
   (c) pharmaceutically acceptable salts thereof, or
   (d) N— or C— derivatives thereof;
   wherein:
   $X_{01}$ is desamino Ser, desamino Ala or desamino Gly; and a pharmaceutically acceptable carrier.

* * * * *

SEQUENCE LISTING

<160> NUMBER OF SEQ ID NOS: 10

<210> SEQ ID NO 1
<211> LENGTH: 34
<212> TYPE: PRT
<213> ORGANISM: Homo sapiens
<220> FEATURE:
<221> NAME/KEY: UNSURE
<222> LOCATION: (1)
<223> OTHER INFORMATION: Can be desamino Ser, desamino Ala, or desamino
      Gly

<400> SEQUENCE: 1

Xaa Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
            20                  25                  30

Asn Phe

<210> SEQ ID NO 2
<211> LENGTH: 34
<212> TYPE: PRT
<213> ORGANISM: Homo sapiens
<220> FEATURE:
<221> NAME/KEY: MOD_RES
<222> LOCATION: (1)
<223> OTHER INFORMATION: Desamino Gly

<400> SEQUENCE: 2

Gly Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
            20                  25                  30

Asn Phe

<210> SEQ ID NO 3
<211> LENGTH: 33
<212> TYPE: PRT
<213> ORGANISM: Homo sapiens
<220> FEATURE:
<221> NAME/KEY: MOD_RES
<222> LOCATION: (1)
<223> OTHER INFORMATION: Desamino Gly

<400> SEQUENCE: 3

Gly Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
            20                  25                  30

Asn

<210> SEQ ID NO 4
<211> LENGTH: 27
<212> TYPE: PRT
<213> ORGANISM: Homo sapiens
<220> FEATURE:
<221> NAME/KEY: MOD_RES
<222> LOCATION: (1)
<223> OTHER INFORMATION: Desamino Gly

<400> SEQUENCE: 4

Gly Val Ser Glu Ile Gln Leu Met His Asn Leu Gly Lys His Leu Asn
 1               5                  10                  15

```
Ser Met Glu Arg Val Glu Trp Leu Arg Lys Lys
            20                  25
```

<210> SEQ ID NO 5
<211> LENGTH: 34
<212> TYPE: PRT
<213> ORGANISM: Homo sapiens
<220> FEATURE:
<221> NAME/KEY: MOD_RES
<222> LOCATION: (1)
<223> OTHER INFORMATION: Desamino Ala

<400> SEQUENCE: 5

```
Ala Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
            20                  25                  30

Asn Phe
```

<210> SEQ ID NO 6
<211> LENGTH: 33
<212> TYPE: PRT
<213> ORGANISM: Homo sapiens
<220> FEATURE:
<221> NAME/KEY: MOD_RES
<222> LOCATION: (1)
<223> OTHER INFORMATION: Desamino Ala

<400> SEQUENCE: 6

```
Ala Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
            20                  25                  30

Asn
```

<210> SEQ ID NO 7
<211> LENGTH: 27
<212> TYPE: PRT
<213> ORGANISM: Homo sapiens
<220> FEATURE:
<221> NAME/KEY: MOD_RES
<222> LOCATION: (1)
<223> OTHER INFORMATION: Desamino Ala

<400> SEQUENCE: 7

```
Ala Val Ser Glu Ile Gln Leu Met His Asn Leu Gly Lys His Leu Asn
 1               5                  10                  15

Ser Met Glu Arg Val Glu Trp Leu Arg Lys Lys
            20                  25
```

<210> SEQ ID NO 8
<211> LENGTH: 34
<212> TYPE: PRT
<213> ORGANISM: Homo sapiens
<220> FEATURE:
<221> NAME/KEY: MOD_RES
<222> LOCATION: (1)
<223> OTHER INFORMATION: Desamino Ser

<400> SEQUENCE: 8

```
Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
            20                  25                  30
```

```
Asn Phe

<210> SEQ ID NO 9
<211> LENGTH: 33
<212> TYPE: PRT
<213> ORGANISM: Homo sapiens
<220> FEATURE:
<221> NAME/KEY: MOD_RES
<222> LOCATION: (1)
<223> OTHER INFORMATION: Desamino Ser

<400> SEQUENCE: 9

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
             20                  25                  30

Asn

<210> SEQ ID NO 10
<211> LENGTH: 27
<212> TYPE: PRT
<213> ORGANISM: Homo sapiens
<220> FEATURE:
<221> NAME/KEY: MOD_RES
<222> LOCATION: (1)
<223> OTHER INFORMATION: Desamino Ser

<400> SEQUENCE: 10

Ser Val Ser Glu Ile Gln Leu Met His Asn Leu Gly Lys His Leu Asn
 1               5                  10                  15

Ser Met Glu Arg Val Glu Trp Leu Arg Lys Lys
             20                  25
```